(12) United States Patent
Fox

(10) Patent No.: US 8,504,498 B2
(45) Date of Patent: Aug. 6, 2013

(54) METHOD OF GENERATING AN OPTIMIZED, DIVERSE POPULATION OF VARIANTS

(75) Inventor: Richard Fox, Kirkwood, MO (US)

(73) Assignee: Codexis, Inc., Redwood City, CA (US)

( * ) Notice: Subject to any disclaimer, the term of this patent is extended or adjusted under 35 U.S.C. 154(b) by 349 days.

(21) Appl. No.: 12/867,429

(22) PCT Filed: Feb. 12, 2009

(86) PCT No.: PCT/US2009/033969
§ 371 (c)(1),
(2), (4) Date: Oct. 21, 2010

(87) PCT Pub. No.: WO2009/102899
PCT Pub. Date: Aug. 20, 2009

(65) Prior Publication Data
US 2011/0029468 A1    Feb. 3, 2011

Related U.S. Application Data

(60) Provisional application No. 61/028,166, filed on Feb. 12, 2008.

(51) Int. Cl.
*G06F 15/18* (2006.01)

(52) U.S. Cl.
USPC .......................................................... 706/13

(58) Field of Classification Search
None
See application file for complete search history.

(56) References Cited

U.S. PATENT DOCUMENTS

| | | |
|---|---|---|
| 5,605,793 A | 2/1997 | Stemmer |
| 5,811,238 A | 9/1998 | Stemmer et al. |
| 5,830,721 A | 11/1998 | Stemmer et al. |
| 5,834,252 A | 11/1998 | Stemmer et al. |
| 6,117,679 A | 9/2000 | Stemmer |
| 6,376,246 B1 | 4/2002 | Crameri et al. |
| 6,586,182 B1 | 7/2003 | Patten et al. |
| 7,603,326 B2 | 10/2009 | Bonabeau et al. |
| 7,783,428 B2 | 8/2010 | Gustafsson et al. |
| 2004/0072245 A1* | 4/2004 | Gustafsson et al. ........... 435/7.1 |
| 2004/0254901 A1* | 12/2004 | Bonabeau et al. ............... 706/13 |
| 2006/0205003 A1 | 9/2006 | Gustafsson et al. |
| 2007/0208677 A1 | 9/2007 | Goldberg et al. |
| 2008/0220990 A1 | 9/2008 | Fox |
| 2009/0312196 A1 | 12/2009 | Colbeck et al. |

FOREIGN PATENT DOCUMENTS

| | | |
|---|---|---|
| EP | 1589463 A1 | 10/2005 |
| WO | 95/22625 A1 | 8/1995 |
| WO | 98/27230 A1 | 6/1998 |

(Continued)

OTHER PUBLICATIONS

Konak, A., Coit D., and Smith A. Multi-objective optimization using genetic algorithms: A tutorial. Reliability Engineering & System Safety. 91 (2006) 992-1007.*

(Continued)

*Primary Examiner* — Kakali Chaki
*Assistant Examiner* — Mario Riojas Ramirez
(74) *Attorney, Agent, or Firm* — Codexis, Inc.

(57) ABSTRACT

The present disclosure relates to methods of rapidly and efficiently searching biologically-related data space to identify a population set maximally diverse and optimized for sets of desired properties. More specifically, the disclosure provides methods of identifying a diverse, evolutionary separated biomolecules with desired properties from complex bio-molecule libraries. The disclosure additionally provides digital systems and software for performing these methods.

4 Claims, 2 Drawing Sheets

FOREIGN PATENT DOCUMENTS

Figure 1:
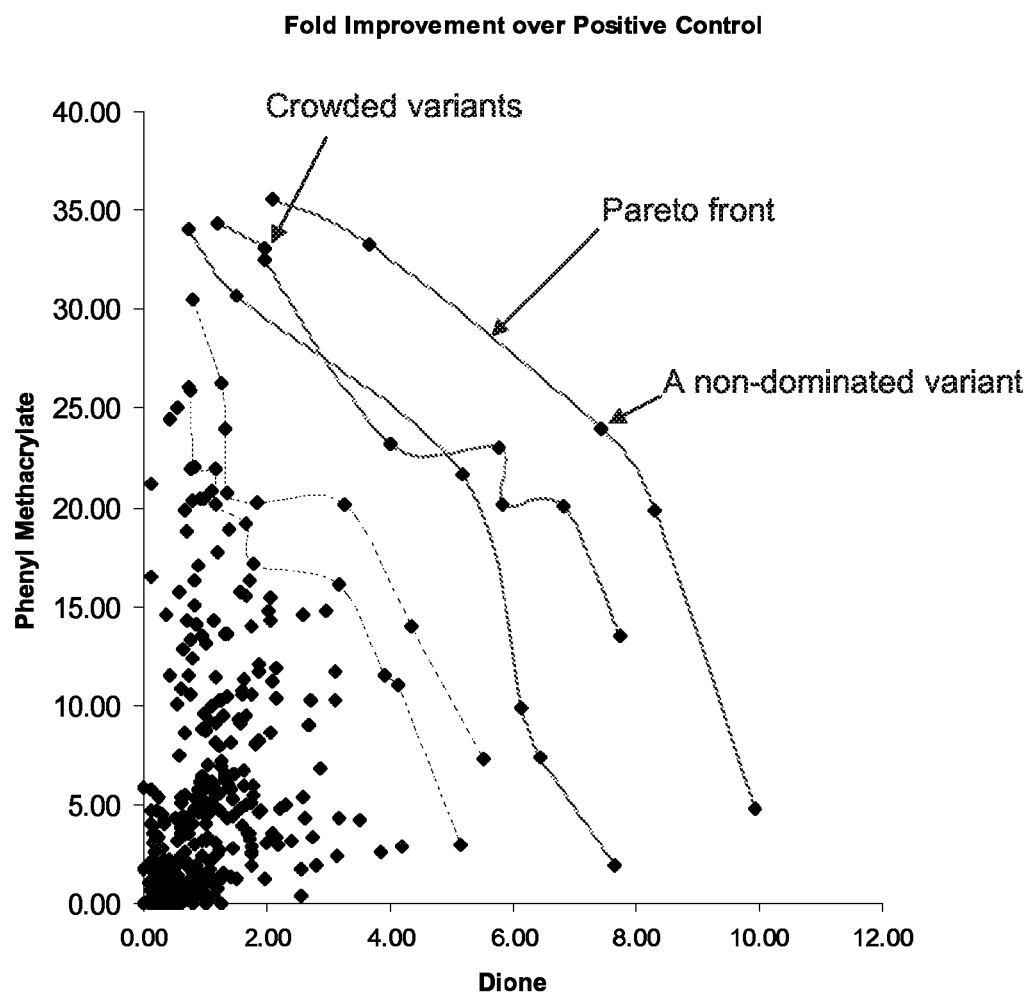

| | | |
|---|---|---|
| WO | 99/29902 A1 | 6/1999 |
| WO | 00/42561 A2 | 7/2000 |
| WO | 02/45012 A2 | 6/2002 |
| WO | 02/075650 A2 | 9/2002 |

OTHER PUBLICATIONS

Altschul, S., et al., "Basic local alignment search tool," J. Mol. Biol., 215: 403-410, 1990.

Altschul, S., et al., "Gapped BLAST and PSI-BLAST: a new generation of protein database search programs," Nucleic Acids Res., 25(17):3389-3402, 1997.

Coello, C., "An Updated Survey of GA-Based Multiobjective Optimization Techniques", ACM Computing Surveys, 32 (2):109-143, 1998.

Darwen, P., et al., "Speciation as automatic categorical modularization," IEEE Transactions on Evolutionary Computation, 1(2):101-108, 1997.

Darwen, P., et al., "Every niching method has its niche: fitness sharing and implicit sharing compared," Proc of Parallel Problem Solving from Nature (PPSN) IV, Vol.1141, Lecture Notes in Computer Science, pp. 398-407,Springer-Verlag, 1996.

Deb, K., "Multiobjective genetic algorithms: problem difficulties and construction of test problems," Evolutionary Computation, 7(3):205-230, 1999.

Elaoud, S., et al., "The Pareto fitness genetic algorithm: Test function study," European Journal of Operational Research 177(1):1703-1719, 2007.

Henikoff, S., et al., "Amino Acid Substitution Matrices from Protein Blocks", Proc. Natl. Acad. Sci. USA, 89:10915-19, 1992.

Horn, J., et al., "A niched pareto genetic algorithm for multiobjective optimization," In Proceedings of the First IEEE Conference on Evolutionary Computation, IEEE World Congress on Computational Computation, 1:82-87, 1994.

Kubo, T., et al., "Enantioselective epoxidation of terminal alkenes to (R)- and (S)-epoxides by engineered cytochromes P450 BM-3," Chemistry, 12(4):1216-20, 2006.

Landwehr, M., et al., "Diversification of catalytic function in a synthetic family of chimeric cytochrome p450s," Chem Biol, 14(3):269-78, 2007.

Needleman, S., et al., "A general method applicable to the search for similarities in the amino acid sequence of two proteins," J. Mol. Biol. 48:443-453, 1970.

Ness, J. et al., "Synthetic shuffling expands functional protein diversity by allowing amino acids to recombine independently," Nature Biotechnology, 20:1251-1255, 2002.

Pearson, W., et al., "Improved Tools for Biological Sequence Comparison," Proc. Natl. Acad. Sci. USA, 85:2444-2448, 1988.

Shukla, P., et al., "On finding multiple Pareto-optimal solutions using classical and evolutionary generating methods", European Journal of Operational Research,181:1630-1652, 2007.

Smith, T., et al., "Comparison of Biosequences," Adv. Appl. Math, 2:482-489, 1981.

Stemmer, W., "DNA Shuffling by Random Fragmentation and Reassembly: In vitro Recombination for Molecular Evolution," Proc. Natl. Acad. Sci. USA, 91:10747-10751, 1994.

* cited by examiner

US 8,504,498 B2

METHOD OF GENERATING AN OPTIMIZED, DIVERSE POPULATION OF VARIANTS

1. CROSS REFERENCE TO RELATED APPLICATION

This application claims the benefit of U.S. Provisional Application No. 61/028,166, filed Feb. 12, 2008, which is hereby incorporated by reference in its entirety.

2. FIELD OF THE INVENTION

The present invention is directed to a method of selecting an optimized diverse population of sets of molecular variants, which can be used for identifying variants displaying altered or improved properties or novel activities. The method creates from a given set of defined variations in polypeptide or polynucleotide sequences (e.g., mutations) a diverse population of variants having maximal information content. The present disclosure further provides a computer-readable media, including program instructions, which when executed by a processor, select a set of molecular variants, a system for selecting a set of molecular variants, a network based system for selecting a set of variants, and the final selected set of molecular variants.

3. BACKGROUND OF THE INVENTION

Various techniques of in silico and in vitro based directed evolution of protein function have allowed the generation of proteins with novel properties. For example, cytochrome p450 enzymes have been evolved to have activity against substrates not normally recognized by the naturally occurring enzyme (see, e.g., Landwehr et al., 2007, Chem Biol 14(3): 269-78; Kubo et al., 2006, Chemistry 12(4):1216-20). Increases in the efficiency of creating polypeptide variants permits the generation of large, diverse population sets that can be screened for new activities. Targeted properties can include, among others, increased enzymatic activity, stereoselectivity, stereo specificity, thermal stability, inhibitor resistance, protease resistance, etc. Generally, selection of the molecular variants for further evolution and screening is done manually following the testing of a set of mutated polypeptides for various desirable and/or undesirable properties, typically based on activity for a single substrate or ligand. This approach to molecular variant selection is time consuming, and subject to the bias of the tester, and therefore may not provide a maximally diverse set for further evolution and testing. In addition, the selection of a diverse population becomes more difficult or intractable as the number and complexity of the variants (e.g., population size) increases, and where a population of variants having different properties, e.g., activities against structurally different substrates or ligands, is being sought. Hence, it is beneficial to have other methods for selecting molecular variants for purposes of testing and evolution of novel biological properties that can manage large sample sizes and diverse sets of performance criteria.

4. SUMMARY OF THE INVENTION

The present disclosure relates to a method of selecting from a plurality of molecular variants an optimized, diverse subset of molecular variants. Generally, the methods herein use Pareto front optimization and nearest neighbor analysis to identify molecular variants optimized, but diverse, with respect to various molecular properties. Generally, the methods comprise the steps of:

(a) selecting one or more objectives for optimization of a plurality of molecular variants, wherein each molecular variant in the plurality is described by two or more objective data;

(b) determining an initial Pareto front membership for each of the plurality of molecule variants based on the objectives of optimization;

(c) setting optimization parameters, wherein the optimization parameters comprise:
  (i) number nvar of molecular variants to create;
  (ii) a molecular variant population size popSize;
  (iii) a crossover rate crossrate;
  (iv) a mutation rate mutrate;
  (v) a fitness function comprising a penalty fitness function and an overall fitness function, wherein the penalty fitness function is based on niche counting and the overall fitness function is based on location in a descending Pareto front divided by the shared number of molecular variants within each front; and
  (vi) specific molecular variants to be included in the nvar of molecular variants; and (d) identifying a search space of acceptable molecular variants by descending from the best Pareto front backward;

(e) generating a random population of genomes of size popSize from the search space of acceptable molecular variants using a selection operator; and (f) selecting a first set of nvar variants by applying a crossover operator, a mutation operator, a repair operator, and a fitness operator to the random population of genomes.

In some embodiments, the method can further comprise repeating step (f) on a combined population of the first nvar set and the molecular variant set popSize to generate a second nvar set.

In some embodiments the methods comprise the steps of:

(a) selecting one or more objectives for optimization of a plurality of molecular variants, wherein each molecular variant in the plurality is described by two or more objective data;

(b) determining an initial Pareto front membership for each of the plurality of molecule variants based on the objectives of optimization;

(c) setting optimization parameters, wherein the optimization parameters comprise:
  (i) number nvar of molecular variants to create;
  (ii) a molecular variant population size popSize;
  (iii) a crossover rate crossrate;
  (iv) number of generations to create nGen;
  (v) a mutation rate mutrate;
  (vi) a fitness function comprising a penalty fitness function and an overall fitness function, wherein the penalty fitness function is based on niche counting and the overall fitness function is based on the location of the molecular variant in a descending Pareto front divided by the shared number of molecular variants within each front; and
  (vii) specific molecular variants to be included in the nvar set of molecular variants;

(d) identifying a search space of acceptable molecular variants by descending from the best Pareto front backward;

(e) generating a random population of genomes of size popSize from the search space of acceptable molecular variants;

(f) selecting a new set of genomes of size popSize from the previous population, wherein each genome consisting of nvar variants is selected by applying a selection operator, a crossover operator, a mutation operator, a repair operator, and a fitness operator to the random population of genomes; and (g) returning the genome with the highest fitness as the final, optimized, diverse nvar set of molecular variants.

In some embodiments, the method can further comprise repeating step (f) nGen times to select new populations of genomes of size popSize.

The present disclosure further provides a computer program comprising a machine readable medium containing the program instructions, such as logic codes, for carrying out the steps of the methods herein. The software for carrying out the steps can be constructed by one of skill using a standard programming language such as Visual Basic, FORTRAN, Basic, Java, or the like.

Further provided are systems for carrying out the methods, where the systems comprise at least one computer comprising a database capable of storing the data set for a list of objective properties, and system software for carrying out each of the steps of the methods above. The system can be part of a stand-alone computer manipulated by a user, or the system can be part of an internet based system, where a server provides the system software for carrying out one or more steps of the method and the client provides user definable information, such as the list of objective for optimization, and values for the various optimization parameters.

In some embodiments, the present methods for selecting an optimized diverse population of molecular variants from a population of molecular variants is used to increase the probability of identifying one or more variants having a desired property.

In some embodiments, the present disclosure provides sets or libraries of molecular variants, such sets containing a diverse set of molecular variants that provides a high degree of information content. The mutations are created such that there is a high probability of creating new molecular variants with improved and/or novel properties.

In some embodiments, the present disclosure provides sets or libraries of molecular variants, optimized with regard to the fitness of each individual molecular variant and/or the fitness of the set, such sets selected from an initial, larger, non-diverse, non-optimized, set of molecular variants.

5. BRIEF DESCRIPTION OF THE FIGURES

FIG. 1 shows a plot of the non-domination and the Pareto optimal front based on the fold improvement versus a positive control for enone-reductase enzymes (ERED) for two different substrates. Non-dominated molecular variants are defined as those molecular variants which are not surpassed in all objectives compared to any other molecular variant. The first Pareto front consists of all non-dominated molecular variants. The second Pareto front is constructed by first removing all molecular variants from the first Pareto front and then running the non-domination classification algorithm on the remaining molecular variants. Subsequent Pareto fronts can be constructed in turn.

Figure 2:
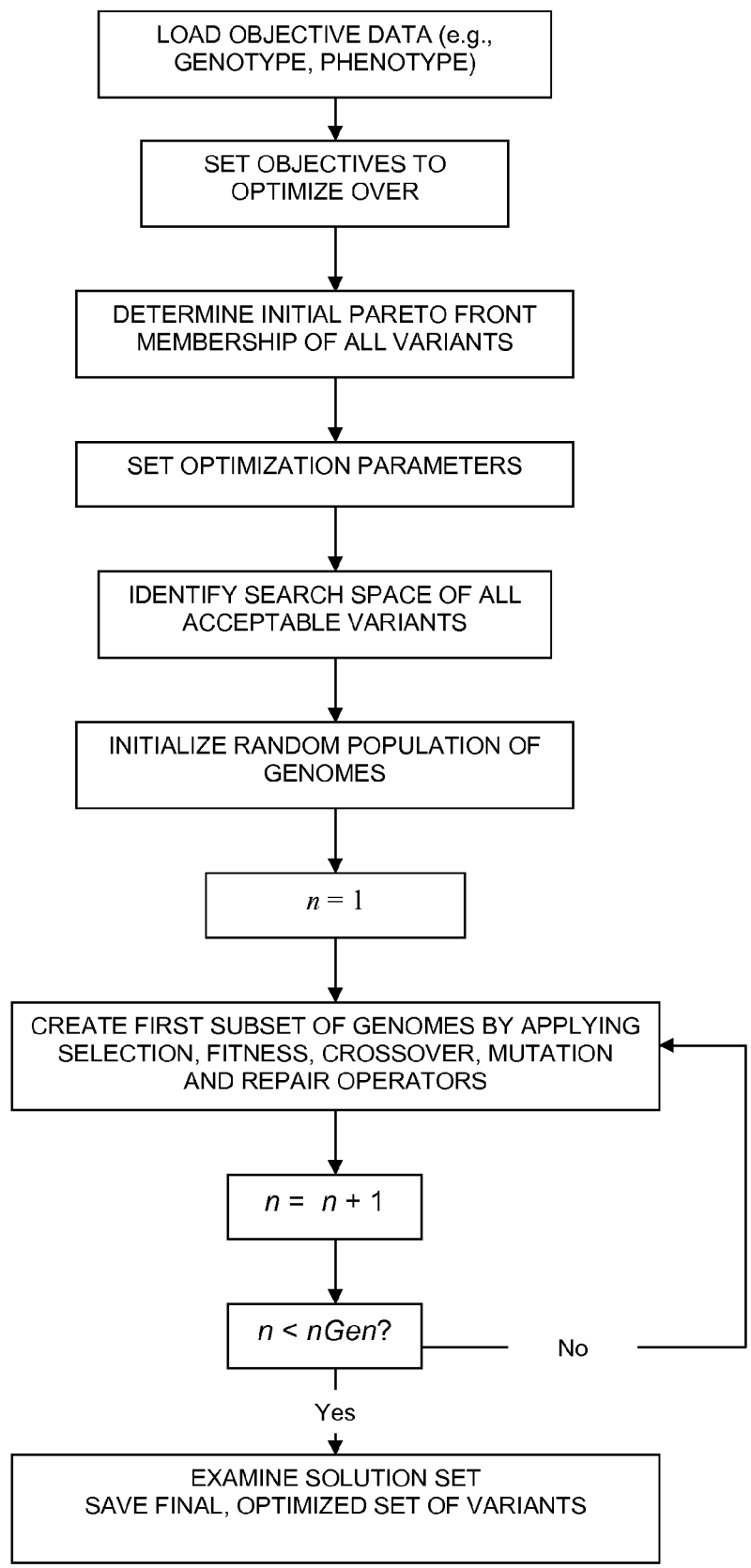

FIG. 2 shows a flow diagram for selecting an optimized subset of maximally diverse molecular variants.

6. DETAILED DESCRIPTION OF THE INVENTION

The present disclosure provides a method of creating a maximally diverse set of molecular variants, which can be used for identifying variants displaying altered properties or novel activities. The method creates from a given set of defined variations (e.g., mutations) a diverse population of variants having maximal information content. In some embodiments the present disclosure provides a method of selecting a diverse subset of molecular variants from an initial, larger, non-optimal set of molecular variants. The present disclosure further provides a computer-readable media, including program instructions, which when executed by a processor, select a set of molecular variants, a system for selecting a set of molecular variants, a network based system for selecting a set of variants, and the final selected set of molecular variants. The following shall apply to the detailed description of embodiments of the method provided herein.

As used in this specification and the appended claims, the singular forms "a", "an" and "the" include plural referents unless the context clearly indicates otherwise. Thus, for example, reference to "a protein" includes more than one protein, and reference to "a compound" refers to more than one compound.

In addition, the use of "or" means "and/or" unless stated otherwise. Similarly, "comprise," "comprises," "comprising," "include," "includes," and "including" are interchangeable and not intended to be limiting.

It is to be further understood that where descriptions of various embodiments use the term "comprising," those skilled in the art would understand that in some specific instances, an embodiment can be alternatively described using the language "consisting essentially of" or "consisting of."

It is to be understood that both the foregoing general description, including the drawings, and the following detailed description, are exemplary and explanatory only, and are not restrictive of this disclosure.

The section headings used herein are for organizational purposes only and not to be construed as limiting the subject matter described.

6.1 DEFINITIONS

"Bio-molecule" refers to a molecule that is generally found in a biological organism, and includes biological macromolecules that are typically polymeric in nature and composed of multiple subunits (i.e., "biopolymers"). Typical bio-molecules include, but are not limited to, molecules that share some structural features with naturally occurring polymers such as an RNAs (formed from ribonucleotide subunits or analogs thereof), DNAs (formed from deoxyribonucleotide subunits or analogs thereof), and polypeptides (formed from amino acid subunits and analogs thereof). Bio-molecules also include, e.g., lipids, carbohydrates, or other organic molecules that can be made by one or more genetically encodable molecules (e.g., one or more enzymes or enzyme pathways) or the like. Bio-molecule also refers to synthetic RNAs, DNAs, and polypeptides that while not naturally occurring, are still capable of biological activity.

"Crossover operator" refers to an operator that determines which parental strand is passed onto the progeny genome during mating of two genomes. It begins with one of two parent genomes, and at every gene locus, which corresponds to a molecular variant, the crossover probability is calculated as the per genome crossover rate divided by the length of the genome. If a uniform random number drawn from the [0,1] scale is less that this per locus probability, then genome copying is switched to the other parental genome. In the context of selecting a maximally diverse subset of variant molecules, the [0,1] designation refers to the absence [0] or presence [1] of the variant molecule in the population set, whether prior to or after application of any fitness function.

"Data structure" refers to the organization and optionally associated device for the storage of information, typically multiple "pieces" of information. The data structure can be a simple recordation of the information (e.g., a list) or the data structure can contain additional information (e.g., annotations) regarding the information contained therein, can establish relationships between the various "members" (i.e., information "pieces") of the data structure, and can provide pointers or links to resources external to the data structure. The data structure can be intangible but is rendered tangible when stored or represented in a tangible medium (e.g., paper, computer readable medium, etc). The data structure can represent various information architectures including, but not limited to simple lists, linked lists, indexed lists, data tables, indexes, hash indices, flat file databases, relational databases, local databases, distributed databases, thin client databases, and the like. In some embodiments, the data structure provides fields sufficient for the storage of one or more character strings. The data structure is optionally organized to permit alignment of the character strings and, optionally, to store information regarding the alignment and/or string similarities and/or string differences. In some embodiments, this information is in the form of alignment "scores" (e.g., similarity indices) and/or alignment maps showing individual subunit (e.g., nucleotide in the case of nucleic acid) alignments. The term "encoded character string" refers to a representation of a biological molecule that preserves desired sequence/structural information regarding that molecule. As noted throughout, nonsequence properties of bio-molecules can be stored in a data structure and alignments of such non-sequence properties, in a manner analogous to sequence based alignment, can be practiced.

"Descriptor" refers to something that serves to describe or identify an item. For example, characters in a character string can be descriptors of amino acids in a polypeptide being represented by the character string. Descriptor can also refer to properties of items, such as the activity of an enzyme on a particular substrate, or the selectivity or solvent stability of a polypeptide.

"Directed evolution" or "artificial evolution" refers to a process of artificially changing a character string (e.g., an amino acid residue on a polypeptide) by artificial selection, recombination, or other manipulation, i.e., which occurs in a reproductive population in which there are (1) varieties of individuals, with some varieties being (2) heritable, of which some varieties (3) differ in fitness (reproductive success determined by outcome of selection for a predetermined property (desired characteristic). The reproductive population can be, e.g., a physical population or a virtual population in a computer system.

"Fitness" refers to the fitness of each genome based on a fitness function, which is applied by a fitness operator. In the present disclosure, the fitness function is designed to maximize the diversity of the newly generated genomes. In some embodiments, fitness can be determined by examining the Pareto front membership of every molecular variant and penalizing those Pareto front member molecular variant fitnesses by dividing by the number of nearest neighbors within a given Pareto front. As such, optimal genomes can consist of molecular variants which are mostly within the first Pareto fronts such that the selected properties are optimized and spread out in an objective space. Additional molecular variants can be selected by identifying molecular variants from descending Pareto fronts and determining the fitness of each molecular variant on the Pareto front.

"Gene" refers to a binary digit representing the presence or absence of a given variant within a genome. For example, in the context of polypeptide variants, the gene represents a polypeptide variant, whose presence or absence in the population is represented by a binary digit; a 0 or a 1. In some embodiments, the gene (character string) represents a set of molecular variants, wherein each gene locus (each character in the string) represents the presence of absence of a molecular variant.

"Genetic algorithms" are processes which mimic evolutionary processes. Genetic algorithms (GAs) are used in a wide variety of fields to solve problems which are not fully characterized or too complex to allow full characterization, but for which some analytical evaluation is available. In other words, GAs are used to solve problems which can be evaluated by some quantifiable measure for the relative value of a solution (or at least the relative value of one potential solution in comparison to another). In the context of the present disclosure, a genetic algorithm is a process for selecting or manipulating character strings in a computer, typically where the character string corresponds to one or more biological molecules (e.g., polynucleotides, polypeptides, or the like).

"Genetic operators" are user-defined operations, or sets of operations, each including a set of logical instructions for manipulating character strings. Genetic operators are applied to cause changes in populations of individuals in order to find interesting (i.e., useful) regions of the search space (populations of individuals with predetermined desired properties) by predetermined means of selection. Predetermined (or partially predetermined) means of selection include computational tools (operators comprising logical steps guided by analysis of information describing libraries of character strings), and physical tools for analysis of physical properties of physical objects, which can be built (synthesized) from matter with the purpose of physically creating a representation of information describing libraries of character strings. In a preferred embodiment, some or all of the logical operations are performed in a digital system. When referring to operations on strings (e.g., recombinations, hybridizations, elongations, fragmentations, segmentations, insertions, deletions, transformations, etc.) it will be appreciated that the operation can be performed on the encoded representation of a biological molecule or on the "molecule" prior to encoding so that the encoded representation captures the operation.

"Genome" refers to a solution set comprised of individual molecular variants, such as a gene or polypeptide. For example, a subset of polypeptide variants can comprise a genome. In some embodiments, a genome is a set of polynucleotide or polypeptide variants, which is represented by a gene or character string, wherein each character in the character string represents the presence or absence of a variant.

"Hyperbox" or "hypervolume" are used interchangeably herein to refer to a selected region in the objective space (e.g., sequence space) that includes at least one individual (e.g., a scored bio-molecule or character string representation of the bio-molecule variant) that lies at least proximate to a Pareto front in a given set of data. A hypervolume can be generated for each molecular variant in the population, and is based on a distance metric in an n-dimensional objective space.

"Library" or "population" is used interchangeably herein to refer to a collection of at least two different molecules and/or character strings (e.g., variants), such as polynucleotide sequences (e.g., genes, nucleic acids, etc.) or encoded products (e.g., polypeptides). A library or population generally includes a large number of different molecules. For example, a library or population typically includes at least about 100 different molecules, at least about 1000 different molecules, and often at least about 10000 or more different molecules.

"Mutation" refers to a difference between a given molecular variant and a reference molecule. For a polynucleotide, the mutations can refer to differences in the nucleotide sequence as compared to a reference polynucleotide, while for a polypeptide, mutations can refer to differences amino acid sequence as compared to a reference polypeptide. Mutations can be represented by changes in the genome as represented by the character string. The number of positions within the molecular variant sequence that can be subject to mutation can be 1 or more, 2 or more, 3 or more, 5 or more, 10 or more, or 20 or more. The number of possible mutations at each position can be 1 or more, 2 or more, 3 or more, 5 or more, 10 or more, or 20 or more. The mutations can correspond to replacement of amino acids or nucleic acids in the reference sequences by other natural or unnatural amino acids or nucleic acids. In some embodiments, "mutations" refers to changes in real polypeptides and polynucleotides. In some embodiments "mutations" refers to changes in the bits of the character strings that represent the genomes.

"Mutation operator" refers to the level of random mutagenesis that can be turned on or off at some defined rate by the user. A candidate genome is mutated by flipping the bit status for a gene in the genome (indicating the presence or absence of a given variant) when a uniform random number is found to be below the per locus mutation rate. In some embodiments, "mutation operator" refers to a genetic operator that changes a single gene in some random, usually small, way. A typical type of mutation is to randomly choose one of the bits in a gene and change its value. Each bit has a probability of being mutated at some specified rate, a mutation rate ("mutrate") defined by the user. Every gene locus is subjected to a low level of random mutagenesis.

"Niche counting" refers to formulating a distance metric in n-dimensional space, where "n" is the number of objectives, and defining a local hypervolume to count the nearest neighbor number of variants contained in the hypervolume or hyperbox. In some embodiments the distance metric is used to create a hypervolume or hyperbox in which the nearest neighbors of a particular variant are contained. Variants with larger numbers of neighbors are penalized. The niche-count is formally defined as $$F = -\sum_{i=1}^{i=n} \frac{1}{nc_i},$$

where $nc_i$ is the niche-count of variant i. The niche-count for each variant is calculated as $$nc_i = \sum_{k=1}^{k=n} c_k, \text{ where } c_k = 1 - \frac{d_{ik}}{\sigma_{share}}$$

for all $d_{ik} < \sigma_{share}$, otherwise $c_k = 0$. The sharing parameter is determined from the transcendental equation $1+n(\sigma_{share})^m - (1+\sigma_{share})^m = 0$. In some embodiments the distance metric is the Euclidian distance. In some embodiments, other distance metrics, such as the Hamming distance, are used.

"Penalty fitness" refers to a penalty value given for the number of neighbors each variant has in the hypervolume (the niche-count), as defined by the defined niche counting method.

"Pareto front" refers to the molecular variants that are non-dominated by other molecular variants. Formal definitions of the Pareto front and algorithms for the determination of the Pareto front can be found in Shuka and Deb (2007) "On finding multiple Pareto-optimal solutions using classical and evolutionary generating methods", *European Journal of Operational Research* 181(3):1017-1724; Coello (1998) "An Updated Survey of GA-Based Multiobjective Optimization Techniques" *ACM Computing Surveys* 32(2):109-143; and Goldberg (1989) "Genetic algorithms in search, optimization and machine learning," Reading, M A, Addison-Wesley, all publications incorporated herein by reference.

"Polynucleotide" refers to deoxyribonucleotides or ribonucleotides and polymers (e.g., nucleic acids, etc.) thereof in either single- or double-stranded form, and is used interchangeably herein with "oligonucleotide" and "nucleic acid." Unless specifically limited, the term encompasses nucleic acids containing known analogs of natural nucleotides which have similar binding properties as the reference nucleic acid. Polynucleotides can be polymers of nucleotides, e.g., A, C, T, U, G, etc. or naturally occurring or artificial nucleotide analogues (e.g., peptide nucleic acid, morpholino nucleic acids, etc.), or a character string representing a polymer of nucleotides, depending on context.

"Polypeptide," "protein," "oligopeptide," and "peptide" are used interchangeably to denote a polymer of at least two amino acids covalently linked by an amide bond, regardless of length or post-translational modification (e.g., glycosylation, phosphorylation, lipidation, myristilation, ubiquitination, etc). Included within this definition are D- and L-amino acids, and mixtures of D- and L-amino acids, and amino acid analogues. As used herein, polypeptide also refers to amino acid sequences represented as character strings.

"Repair operator" refers to an operator used to enforce constraints on progeny genomes. In particular, the number nvar of molecular variants to be selected as a plurality of molecular variants is a fixed number, and any genome solution must ensure that the desired number of bits (variants) be turned on. The repair operator enforces the nvar constraint by randomly turning off (on) bits if there are too many (little) bits to begin with.

"Screening" refers to the process in which one or more properties of one or more bio-molecules are determined. For example, typical screening processes include those in which one or more properties of one or more members of one or more libraries is/are determined. Biomolecules can be screened for thermal stability, solvent stability, activity in performing a chemical reaction, selectivity in performing a chemical reaction, and other properties known in the art.

"Selection" refers to the process in which one or more molecular variants are identified as having one or more properties of interest. Thus, for example, one can screen a library to determine one or more properties of one or more library members. If one or more of the library members is/are identified as possessing a property of interest, it is selected. Selection can refer to physical selection, or in silico selection. In preferred embodiments, selection is based on the application of Pareto Front Optimization and Genetic Algorithms to find molecular variants with preferred properties.

"Selection operator" refers to a tournament selection operator which is used to select a genome from a population of genomes. The first parent is identified by selecting two genomes at random from a population set and the genome with higher fitness is selected for breeding. The other parent is determined in the same fashion.

"Sequence," and "character string" are used interchangeably herein to refer to the order and identity of amino acid residues in a protein (i.e., a protein sequence or protein character string) or to the order and identity of nucleotides in a nucleic acid (i.e., a nucleic acid sequence or nucleic acid character string), as encoded by a string of characters or numbers.

"Percentage of sequence identity" and "percentage homology" are used interchangeably herein to refer to comparisons among polynucleotides and polypeptides, and are determined by comparing two optimally aligned sequences over a comparison window, wherein the portion of the polynucleotide or polypeptide sequence in the comparison window may comprise additions or deletions (i.e., gaps) as compared to the reference sequence (which does not comprise additions or deletions) for optimal alignment of the two sequences. The percentage may be calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity. Alternatively, the percentage may be calculated by determining the number of positions at which either the identical nucleic acid base or amino acid residue occurs in both sequences or a nucleic acid base or amino acid residue is aligned with a gap to yield the number of matched positions, dividing the number of matched positions by the total number of positions in the window of comparison and multiplying the result by 100 to yield the percentage of sequence identity. Those of skill in the art appreciate that there are many established algorithms available to align two sequences. Optimal alignment of sequences for comparison can be conducted, e.g., by the local homology algorithm of Smith and Waterman, 1981, *Adv. Appl. Math.* 2:482, by the homology alignment algorithm of Needleman and Wunsch, 1970, *J. Mol. Biol.* 48:443, by the search for similarity method of Pearson and Lipman, 1988, *Proc. Natl. Acad. Sci. USA* 85:2444, by computerized implementations of these algorithms (GAP, BESTFIT, FASTA, and TFASTA in the GCG Wisconsin Software Package), or by visual inspection (see generally, Current Protocols in Molecular Biology, F. M. Ausubel et al., eds., *Current Protocols*, Greene Publishing Associates, Inc. and John Wiley & Sons, Inc., (1995 Supplement)). Examples of algorithms that are suitable for determining percent sequence identity and sequence similarity are the BLAST and BLAST 2.0 algorithms, which are described in Altschul et al., 1990, *J. Mol. Biol.* 215: 403-410 and Altschul et al., 1977, *Nucleic Acids Res.* 3389-3402, respectively. Software for performing BLAST analyses is publicly available through the National Center for Biotechnology Information website. This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al, supra). These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, M=5, N=−4, and a comparison of both strands. For amino acid sequences, the BLASTP program uses as defaults a wordlength (W) of 3, an expectation (E) of 10, and the BLOSUM62 scoring matrix (see Henikoff and Henikoff, 1989, *Proc. Natl. Acad. Sci. USA* 89:10915).

The degree of percent amino acid sequence identity can also be obtained by ClustalW analysis (version W 1.8) by counting the number of identical matches in the alignment and dividing such number of identical matches by the length of the reference sequence, and using the following default ClustalW parameters to achieve slow/accurate pairwise optimal alignments—Gap Open Penalty: 10; Gap Extension Penalty: 0.10; Protein weight matrix: Gonnet series; DNA weight matrix: IUB; Toggle Slow/Fast pairwise alignments=SLOW or FULL Alignment.

Exemplary determination of sequence alignment and % sequence identity can employ the BESTFIT or GAP programs in the GCG Wisconsin Software package (Accelrys, Madison Wis.), using default parameters provided, or the ClustalW multiple alignment program (available from the European Bioinformatics Institute, Cambridge, UK), using, in some embodiments, the parameters above.

6.2 METHOD OF SELECTING A SET OF OPTIMIZED, DIVERSE VARIANTS

The present disclosure provides a method of using Pareto front optimization and Genetic Algorithms to select molecular variants that are maximized for diversity with respect two or more properties of the variant population. For example, in a search for polypeptide variants acting on ligands not normally recognized by the naturally occurring polypeptide, a diverse set of molecular variants can be tested for activity, and then a candidate variant chosen based on one or more different criteria for further evolution. This process can result in identification of polypeptides acting more efficiently on the ligand than the reference polypeptide, such as a naturally occurring polypeptide. Screening a diverse set of molecular variants for a desired, often novel activity, can provide an initial set of polypeptides for further evolution and selection. A population set of maximally diverse polypeptides can enhance the probability of identifying a starting polypeptide backbone for further evolution, particularly if the activity in question is novel to the reference enzyme. Generally, this process of selecting a diverse set of variants is carried out manually, which can limit the ability to select the most diverse of species for testing of the improved or novel activities. However, the number of possible sets of molecular variants that can be selected from a screened variant library is far too large to search exhaustively for the optimal solution. The problem is it is not reducible to any polynomial time algorithm (Sipser, M., 2005, *Introduction to the Theory of Computation*, 2nd Ed., Course Technology) as the fitness of a solution depends, in general, on the fitnesses of the all other variants present. Thus, multi-objective optimization cannot be done by "hand" or by brute-force methods. Fortunately, evolutionary methods such as genetic algorithms (GAs) are well suited to finding optimized solutions to problems with such extreme combinatorial complexity (Goldberg, D. E., 1989, *Genetic Algorithms in Search, Optimization, and Machine Learning*; incorporated herein by reference). The present disclosure provides a method of selecting a set of molecular variants to maximize its diversity for two or more traits or objectives by excluding variants which are similar to each other. While the application of the method is illustrated for a bioactive polypeptide, e.g., an enzyme, it is to be understood that the method can be applied to any type of molecule that can be screened for two or more different properties.

Generally, the present disclosure uses a Pareto front determined for a population of molecular variants, and a fitness function to select out variants based on the number of nearest neighbors shared between variants in the Pareto front. By use of a descending Pareto front and nearest neighbor analysis for each variant on the descending Pareto front, variants that are similar to each other can be screened out, thereby resulting in an optimized, diverse set of molecular variants that can be used as a set for initial screening for other improved or novel properties.

In view of the foregoing, in some embodiments, the method for selecting an optimized, diverse population of molecular variants comprises:

(a) selecting one or more objectives for optimization of a plurality of molecular variants, wherein each molecular variant in the plurality is described by two or more objective data;

(b) determining a first Pareto front membership for each of the plurality of molecule variants based on the objectives of optimization;

(c) setting optimization parameters, wherein the optimization parameters comprise:
  (i) number nvar of molecular variants to select;
  (ii) a molecular variant population size popSize;
  (iii) a crossover rate crossrate;
  (iv) a mutation rate mutrate;
  (v) a fitness function comprising a penalty fitness function and an overall fitness function, wherein the penalty fitness function is based on niche counting and the overall fitness function is based on location in a descending Pareto front divided by the number of shared molecular variants within each front; and
  (vi) molecular variants to be included in the nvar of molecular variants; and (d) identifying a search space of acceptable variants;

(e) generating a random population of genomes from the search space of acceptable variants using a selection operator; and (f) selecting a first set of nvar variants by applying a crossover operator, a mutation operator, a repair operator, and a fitness operator to the random population of genomes.

In some embodiments, the method can further comprise repeating step (f) nGen times to select new populations of genomes of size popSize.

In some embodiments, the method for selecting an optimized, diverse population of molecular variants comprises:

(a) selecting one or more objectives for optimization of a plurality of molecular variants, wherein each molecular variant in the plurality is described by two or more objective data;

(b) determining an initial Pareto front membership for each of the plurality of molecule variants based on the objectives of optimization;

(c) setting optimization parameters, wherein the optimization parameters comprise:
  (i) number nvar of molecular variants to create;
  (ii) a molecular variant population size popSize;
  (iii) a crossover rate crossrate;
  (iv) number of generations to create nGen;
  (v) a mutation rate mutrate;
  (vi) a fitness function comprising a penalty fitness function and an overall fitness function, wherein the penalty fitness function is based on niche counting and the overall fitness function is based on the location of the molecular variant in a descending Pareto front divided by the shared number of molecular variants within each front; and
  (vii) specific molecular variants to be included in the nvar set of molecular variants; and (d) identifying a search space of acceptable molecular variants by descending from the best Pareto front backward;

(e) generating a random population of genomes of size popSize from the search space of acceptable molecular variants;

(f) selecting a new set of genomes of size popSize from the previous population, wherein each genome consisting of nvar variants is selected by applying a selection operator, a crossover operator, a mutation operator, a repair operator, and a fitness operator to the random population of genomes; and (g) returning the genome with the highest fitness as the final, optimized, diverse set of molecular variants.

In some embodiments, the method can further comprise repeating step (f) nGen times to select new populations of genomes of size popSize.

In various embodiments, the two or more desired properties (i.e., objective data) can be any properties of the molecular variant. For purposes of illustration, if the molecular variant is a polypeptide that has an enzymatic activity, the objective data can correspond to any number of properties associated with the activity of the polypeptide, including, among others, stereoselectivity, stereospecificity, solvent stability, pH stability, inhibitor resistance, substrate conversion, etc.

In some embodiments, where the molecular variant is an enzyme, the desired properties or objectives can be activity on two or more structurally different substrates. The substrates can have the same or different functional groups. In some embodiments, the polypeptides are derived from a parental reference sequence, where the polypeptides have been mutated such that the population of variants can act on a variety of different substrates. The number of substrates tested can be 2 or more, 3 or more, 4 or more, 5 or more, 6 or more, 7 or more, 8 or more, 10 or more, or 20 or more.

In some embodiments, the plurality of molecular variants can be part of a library or population of variants. For a plurality of polypeptide variants, the library may include proteins from various sources, such as naturally occurring proteins of different protein families, such as different enzyme classes. In some embodiments, the polypeptide members can consist of a polypeptides encoded by members of a single gene family. In some embodiments, the members include polypeptides obtained by using a recombination-based diversity generation mechanism, (e.g., DNA fragmentation-mediated recombination, synthetic oligonucleotide-mediated recombination). Typically, the polypeptide variant library is generated from polynucleotides encoding one or more naturally occurring proteins using DNA shuffling and other diversity generating procedures, such as those described in Stemmer, 1994, *Proc. Natl. Acad. Sci. USA* 10747-10751; Ness et al., 2002, *Nature Biotechnology* 20:1251-1255; WO 95/22625; WO 00/42561; WO/42832; WO 98/27230; WO 99/29902; U.S. Pat. No. 5,811,238; U.S. Pat. No. 5,605,793; U.S. Pat. No. 5,830,721; and U.S. Pat. No. 5,834,252; publications incorporated herein by reference. In some embodiments, the library is generated by systematically varying individual residues, such as residues in the substrate binding pocket or catalytic site of an enzyme. Oligonucleotides can be designed which contain the nucleotides required to assemble the diversity present in the plurality of polynucleotides. The polynucleotides encoding the variant polypeptide sequences are then transcribed and translated, either in vitro or in vivo, to create a set or library of protein variant sequences.

For each variant in the library or variant population, there are one or more objective data, which describe properties of the molecular variants, as described above. The objective data can include sequence information, which can be characterized in character strings, and/or other properties of the variant, such as activity data. Activity data may be obtained by assays or screens appropriately designed to measure activity magnitudes. Such techniques are well known and are not central to application of the method. For polypeptides with biological activity, e.g., enzymes, the principles for designing appropriate assays or screens are widely understood, and will depend on the type of enzyme, and the desirable properties of the polypeptides. The activity used in the method herein can be protein stability (e.g., thermal or solvent stability), catalytic activity (particularly on structurally different substrates), stereospecificity, stereoselectivity, inhibitor resistance, toxicity, and the like. High throughput assays are particularly suitable for screening polypeptide libraries. For example, each well of a microtiter plate can be used to run a separate assay, or, if concentration or incubation time effects are to be observed, every 5-10 wells can test a single variant (e.g., at different concentrations). Thus, a single standard microtiter plate can assay about 100 (e.g., 96) reactions. It is possible to assay several different plates per day; assay screens for up to about 6,000-20,000 different assays (i.e., involving different nucleic acids, encoded proteins, concentrations, etc.) are possible using the integrated systems. In other embodiments, microfluidic approaches to reagent manipulation have been developed, e.g., by Caliper Technologies (Mountain View, Calif.), which can provide very high throughput microfluidic assay methods. The mutations associated with a particular protein variant characterized by one or more different properties are readily determined from expression libraries by sequencing the polynucleotide encoding the variant polypeptides. In this manner, the variant polypeptides, as defined by their unique sequences, and their associated biological properties of the polypeptide, can be obtained.

Once the objective data for the plurality of molecular variants are determined and inputted, a first Pareto front membership for each of the plurality of molecule variants is calculated based on the selected objectives of optimization. Generally, Pareto front optimization is a multi-objective evolutionary algorithm that simultaneously improves two or more desired objectives. The Pareto front is occupied by molecular variants that are non-dominated by other molecular variants in at least one of two or more desired objectives. In other words, the solutions, typically represented by the numbered data points that lie on the Pareto front represent trade-off solutions that are not "dominated" by any other solution. These non-dominated points are defined by the fact that no other solution exists in the hypothetical data set that is better than all solutions in both objectives. FIG. 1 shows a example of a Pareto front determined for a set of related enone reductase (ERED) enzymes having different values for their fold improvement in activity versus a positive control for two substrates (Dione and Phenyl Methacrylate). The Pareto front can be established by any number of ways known in the art. See US application publication Nos. 20040072245; 20060195204; 20060205003 and 20070208677. Other applications of Pareto fronts for purposes of multiobjective optimization are described in WO 02/075650; Shukla and Deb, 2007, *European Journal of Operational Research* 181(3): 1017-1724; and Elaoud and Loukil, 2007, *European Journal of Operational Research* 177(1):1703-1719; all references incorporated herein by reference.

A set of optimization parameters is defined, where the parameters comprise:
(i) the number of molecular variants nvar to be created;
(ii) a molecular variant population size popSize;
(iii) a crossover rate crossrate;
(iv) number of generations to create nGen;
(v) a mutation rate mutrate;
(vi) an fitness function; and
(vii) specific molecular variants to be automatically included in the solution set nvar.

The number of molecular variants to be created, nvar, is a finite number defined by the user, and constrains the size of the final solution. The value can be set based on any number of criteria, such as the number of variants that can be efficiently screened for the various properties of the molecular variants. For example, a straightforward nvar can correspond to the number of samples in a selected number of 96-well plates that can be initially screened efficiently.

The population size popSize is simply the initial starting population of random genomes (number of sets of nvar molecular variants) chosen for processing for fitness and other operations.

The crossover rate crossrate is the probability of crossover between two members in the molecular variant population and is applied by a crossover operator. A crossover operator generally pairs members of the population, and the different parts of a "gene" are cross-combined, resulting in a pair of offspring, i.e., a new pair of solutions. A variety of crossover operators that have been developed in the field of genetic algorithms can be used, such as, for example, one point, multipoint, uniform, and arithmetic, each offering different performance (in terms of convergence, or the exploration/exploitation tradeoff) under different conditions. In the context of the present disclosure, the crossover rate is based on the [0,1] scale and refers to the absence or presence of the variant molecule in the population set, whether prior to or after application of any fitness operator.

The mutation rate mutrate is applied to a population by a mutation operator, and acts to create, with some defined probability, a change in the character strings of the "gene" (e.g., polypeptide) or "genome" and functions to maintain diversity within the population.

The fitness function assesses the fitness of a particular molecular variant and comprises a penalty fitness function and an overall fitness function. The penalty fitness function takes into account the number of nearest neighbors, and is based on the reasoning that molecular variants similar to each other are less likely to show different behaviors or novel properties. Although molecular variants could be scored solely based on membership within each Pareto front, and selected based on their isolation in the Pareto front, this type of selection is more useful for selecting a single molecular variant for further optimization of a defined property, as opposed to identification of a set of optimized, maximally diverse molecular variants. As such, molecular variants on the Pareto front are selected for fitness by penalizing molecular variants which are similar to each other. The penalty fitness function can be determined using the concept of niche counting, which counts the number of nearest neighbor molecular variants in the objective space. Generally, niche counting consists of formulating a distance metric in an n-dimensional space, where n is the number of objectives, using the distance to define a local hypervolume, and then counting the number of nearest neighbor variants occupying the hypervolume. A nearest neighbor molecular variant located further from a molecular variant occupies a smaller fraction of the hypervolume space with respect to that molecular variant. Solutions that contain molecular variants with a higher number of nearest neighbors, i.e., large number of molecular variants occupying the hypervolume space, are less fit solutions. Because the number nvar is finite, the algorithm tends to select one molecular variant from the crowd of similar molecular variants. The details of formulating the distance metric and niching are described in Deb, K., 1999, "Multiobjective genetic algorithms: problem difficulties and construction of test problems,"*Evolutionary Computation* 7:205-230; incorporated herein by reference. Other niche techniques are described in Darwen et al., 1997, "Speciation as automatic categorical modularization," *IEEE Transactions on Evolutionary Computation* 1(2):101-108; Darwen et al., 1996, "Every niching method has its niche: fitness sharing and implicit sharing compared," *Proc. of Parallel Problem Solving from Nature* (PPSN) IV, Vol. 1141, Lecture Notes in Computer Science, pp. 398-407, Springer-Verlag; and Horn et al., 1994, "A niched pareto genetic algorithm for multiobjective optimization," In *Proceedings of the First IEEE Conference on Evolutionary Computation*, IEEE World Congress on Computational Computation, 1:82-87; all publications incorporated herein by reference.

A second aspect of the fitness function is the overall fitness function, which in the present disclosure can consist of assigning molecular variants to descending Pareto fronts and dividing those fitnesses by the number of shared neighbors, as determined by the distance metric and niche count. Ever descending Pareto fronts represent lower fitness levels (e.g., less optimal). The overall fitness function can be used to drive the optimization to select the best subset of variants from the plurality of molecular variants.

The specific molecular variants to be automatically included in the solution nvar can comprise particular sets of molecular variants known to have predetermined characteristics useful for the objectives, such as expanded substrate specificity. In some cases there can be zero of such particular molecular variants to be included in the solution set.

Although the optimization parameters are described for Pareto front optimization genetic algorithms, it is to be understood that other strategies may be used, including, among others, tabu search, simulated annealing, etc.

To identify a search space for selecting a set of optimized, diverse molecular variants, descending Pareto fronts are used to identify molecular variants less fit than those in the initial Pareto front, but which can provide diversity for the selected size nvar. From this superset of molecular variants, an initial random population of genomes of size popSize is generated by a selection operator. The genomes represent the solution set of molecular variants from which the set of optimized, diverse molecular variants are chosen.

To select a set of optimized, diverse molecular variants from the initial population popSize, the random plurality of genomes is subjected to selection based on genetic operators that include a crossover operator, mutation operator, fitness operator, and repair operator. These operators act to apply the corresponding optimization parameters discussed above to the random plurality of genomes. In the present disclosure, the repair operator is used to place constraints on the selection by limiting the size of the progeny genome to a user-defined finite number nvar. If the progeny genome size is less than nvar, the repair operator enforces the constraint by turning bits on to generate additional molecular variants to satisfy nvar. If the size of the progeny population is greater than nvar, the repair operator enforces the constraint by turning bits off to reduce the number of molecular variants to satisfy nvar.

The set of molecular variants resulting from application of the optimization parameters and corresponding operators is evaluated for the desired properties as well as diversity. For purposes of illustration, a set of resulting polypeptide variants can be generated by recombinant techniques, and each variant expressed in an appropriate expression system, either in vitro or in vivo. The synthesized polypeptides are evaluated for the desired properties, such as activity, stability and other profiles. If it is desirable to obtain additional optimized, diverse sets of molecular variants, the process of applying the optimization parameters can be reiterated to generate a second set of nvar. As such, the nvar number of variants can be combined with all the candidates from the original superset in order to create a single subset nvar. In this way, the overall diversity comparing all variants against each other will be maximized. Continued reiteration for a number of generations nGen allows evaluation of a number of different solutions sets of molecular variants for further evaluation, in silico or in the laboratory.

The method herein can be used alone or in conjunction with other methods, such as methods of creating an optimized diverse population of molecules. In other words, an initial optimized diverse set of variant polypeptides could be generated and tested using the methods described herein, and based on the initial sets of identified mutations, additional polypeptide variants created to further evolve other variants to screen for the desired properties. Methods for creating additional variants, both in silico and in the laboratory, for screening are described in US application publications 20040072245, 20060195204, 20060205003, and 20070208677, all of which are incorporated herein by reference.

6.3 COMPUTER IMPLEMENTATION AND SYSTEMS

The present disclosure further provides the method above in the form of computer software to implement the method in a computer. Generally, the computer program product comprises a machine readable storage medium having program instructions comprising:

(a) code for receiving an objective data set representing two or more properties of each molecular variant;

(b) code for generating a first Pareto front membership of all molecular variants based on the one or more objectives for optimization;

(c) code for setting optimization parameters, wherein the optimization parameters comprise:
  (i) number nvar of molecular variants to create;
  (ii) a molecular variant population size popSize;
  (iii) a crossover rate crossrate;
  (iv) a mutation rate mutrate;
  (vi) a fitness function comprising a penalty fitness function and an overall fitness function, wherein the penalty fitness is based on niche count and the overall fitness function is based on location in a descending Pareto front divided by the number of shared number of molecular variants within each front; and
  (vii) specific molecular variants to be automatically included in the solution set nvar; and (d) code for identifying a search space of acceptable variants;

(f) code for generating a random population of genomes from the search space of acceptable variants by applying a selection operator; and (e) code for applying a set of operators comprising a crossover operator, a mutation operator, a fitness operator, and a repair operator on the random plurality of genomes to select a set nvar of optimized diverse molecular variants.

In some embodiments, the computer software further comprises a code for reiterating step (e) on a combination of the first nvar set and the initial population popSize to generate a second nvar set of optimized diverse molecular variants, as discussed above. The computer program can further comprise a code for reiteratively performing step (e) for nGen number of generations to generate additional sets of optimized diverse molecular variants.

In some embodiments, the computer program product comprises a machine readable storage medium having program instructions comprising:

(a) code for receiving an objective data set representing two or more properties of each molecular variant;

(b) code for generating a first Pareto front membership of all molecular variants based on the one or more objectives for optimization;

(c) code for setting optimization parameters, wherein the optimization parameters comprise:
   (i) number nvar of molecular variants to create;
   (ii) a molecular variant population size popSize;
   (iii) a crossover rate crossrate;
   (iv) number of generations to create nGen;
   (v) a mutation rate mutrate;
   (vi) a fitness function comprising a penalty fitness function and an overall fitness function, wherein the penalty fitness is based on niche counting and the overall fitness function is based on the location of the molecular variant in a descending Pareto front divided by the shared number of molecular variants within each front; and
   (vii) specific molecular variants to be included in the solution set nvar; and (d) code for identifying a search space of acceptable molecular variants by descending from the best Pareto front backward;

(e) code for generating a random population of genomes from the search space of acceptable molecular variants;

(f) code for selecting a new set of genomes of size popSize from the previous population, wherein each genome consisting of nvar molecular variants is selected by applying a selection operator, a crossover operator, a mutation operator, a repair operator, and a fitness operator to the random population of genomes; and (g) code for returning the genome with the highest fitness as the final, optimized, diverse nvar set of molecular variants.

In some embodiments, the computer program can further comprise code for repeating step (f) nGen times to select new populations of genomes of size popSize.

The computer program can further comprise a code for displaying information about the completed selection of molecule variants on an output device. This information can include the identification numbers of the molecular variants included in the final set, their sequences, their fitness, their niche counts, and the values of their associated objective data.

The computer-readable storage medium can be any storage medium, such as, for example, semiconductor memory devices (e.g., ROM), CD-ROM, memory key, flash memory card, diskette, magnetic tape, having stored thereon a program which, when executed in a computing environment, provides for implementation of algorithms to carry out all or a portion of the methods above. Where the computer-readable medium contains a complete program for carrying out the methods described herein, the program includes program instructions for collecting, analyzing and generating output, and generally includes computer readable code devices for interacting with a user as described herein, and processing the input data. In addition, embodiments of the computer-implemented method also relate to computer readable media or computer program products that include program instructions and/or data (including data structures) for delivering and performing various computer implemented operations. Examples of program instructions include both low-level code, such as produced by a compiler, and files containing higher level code that may be executed by the computer using an interpreter. Further, the program instructions include machine code, source code and any other code that directly or indirectly controls operation of a computing machine in accordance with this invention. The code may specify the input, output, calculations, conditionals, branches, iterative loops, etc.

In various embodiments, standard desktop applications such as word processing software (e.g., Microsoft Word™ or Corel WordPerfect™) and database software (e.g., spreadsheet software such as Microsoft Excel™, Corel Quattro Pro™, or database programs such as Microsoft Access™ or Paradox™) can be adapted to the embodiments herein by inputting one or more character strings into the software which is loaded into the memory of a digital system, and performing an operation as noted herein on the character string. For example, systems can include the foregoing software having the appropriate character string information, e.g., used in conjunction with a user interface (e.g., a GUI in a standard operating system such as a Windows, Macintosh or LINUX system) to manipulate strings of characters.

Further provided herein are systems for selecting an optimized, diverse set of molecular variants from a plurality of molecular variants, comprising:

(a) at least one computer comprising a database capable of storing an objective data set representing two or more properties of each molecular variant in a plurality of molecular variants; and (b) system software comprising one or more logic instructions for:
   (i) receiving an objective data set representing two or more properties of each molecular variant;
   (ii) generating a first Pareto front membership of all molecular variants based on the one or more objectives for optimization;
   (iii) setting optimization parameters, wherein the optimization parameters comprise:
      (a) number nvar of molecular variants to create;
      (b) a molecular variant population size popSize;
      (c) a crossover rate crossrate;
      (d) a mutation rate mutrate;
      (e) a fitness function comprising a penalty fitness function and an overall fitness function, wherein the penalty fitness is based on niche count and the overall fitness function is based on location in a descending Pareto front divided by the shared number of molecular variants within each front; and
      (f) specific molecular variants to be automatically included in the solution set nvar; and
   (iv) identifying a search space of acceptable variants;
   (v) generating a random population of genomes from the search space of acceptable molecular variants by applying a selection operator; and
   (vi) applying to the random population of molecular variants a set of operators comprising a selection operator, a crossover operator, a mutation operator, a fitness operator, and a repair operator to select a set nvar of optimized, diverse molecular variants.

In some embodiments, the invention provides systems for selecting an optimized, diverse set of molecular variants from a plurality of molecular variants, comprising:

(a) at least one computer comprising a database capable of storing an objective data set representing two or more properties of each molecular variant in a plurality of molecular variants; and (b) system software comprising one or more logic instructions for:

(i) receiving an objective data set representing two or more properties of each molecular variant;

(ii) generating a first Pareto front membership of all molecular variants based on the one or more objectives for optimization;

(iii) setting optimization parameters, wherein the optimization parameters comprise:

(a) number nvar of molecular variants to create;
(b) a molecular variant population size popSize;
(c) a crossover rate crossrate;
(d) number of generations to create nGen;
(e) a mutation rate mutrate;
(f) a fitness function comprising a penalty fitness function and an overall fitness function, wherein the penalty fitness is based on niche counting and the overall fitness function is based on the location of the molecular variant in a descending Pareto front divided by the shared number of molecular variants within each front; and
(g) specific molecular variants to be automatically included in the solution set nvar; and (iv) identifying a search space of acceptable molecular variants by descending from the best Pareto front backward;

(v) generating a random population of genomes from the search space of acceptable molecular variants;

(vi) selecting a new set of genomes of size popSize from the previous population, wherein each genome consisting of nvar molecular variants is selected by applying a selection operator, a crossover operator, a mutation operator, a repair operator, and a fitness operator to the random population of genomes; and (c) returning the genome with the highest fitness as the final, optimized, diverse nvar set of molecular variants.

In some embodiments, system software further comprises one or more logic instructions for repeating step (vi) nGen times to select new populations of genomes of size popSize.

In various embodiments, the computer of the systems typically include, e.g., a digital computer with the software for performing the various steps of the method. The computer can be, e.g., a PC (Intel x86 or Pentium chip-compatible DOS™, OS2™, WINDOWS™, WINDOWS95™, WINDOWS98™, LINUX, Apple-compatible, MACINTOSH™ compatible, Power PC compatible, or a UNIX compatible (e.g., SUN™ work station or machine) or other common commercially-available computer known in the art. The software for carrying out the steps can be constructed by one of skill using a standard programming language such as Visual Basic, FORTRAN, Basic, Java, or the like, according to the methods herein. Any controller or computer optionally includes a monitor which can include, e.g., a cathode ray tube ("CRT") display, a flat panel display (e.g., active matrix liquid crystal display, liquid crystal display), or others. Computer circuitry is often placed in a box which includes numerous integrated circuit chips, such as a microprocessor, memory, interface circuits, and others. The box also optionally includes a hard disk drive, a floppy disk drive, a high capacity removable drive such as a writeable CD-ROM, and other common peripheral elements. Inputting devices such as a keyboard, touch screen, or mouse optionally provide for input from a user and for user selection of sequences to be compared or otherwise manipulated in the relevant computer system. Display devices provide a means of monitoring of the selection of the molecular variants as well as providing details of the set of molecular variants created. These details include the mutations determined for each molecular variant, the frequencies of each mutation, and the information content of the set of molecular variants.

The computer also includes appropriate software for receiving user instructions, either in the form of user input into a set parameter fields, e.g., in a GUI, or in the form of preprogrammed instructions, e.g., preprogrammed for a variety of different specific operations. The software then converts these instructions to appropriate language for instructing the system to carry out any desired operations. The digital system can also include output elements for displaying the results of the method.

In some embodiments, the computer implemented method for selecting an optimized, diverse set of molecular variants from a plurality of molecular variants, can comprise:

(a) inputting and storing an objective data set representing two or more properties of each molecular variant in a plurality of molecular variants in a first computer memory;

(b) retrieving and processing the input of (a) with a computer microprocessor, wherein the microprocessor applies a computer program that generates a first Pareto front membership of all molecular variants based on the one or more objectives for optimization;

(c) inputting and storing optimization parameters in a second computer memory, wherein the optimization parameters comprise:

(i) number nvar of molecular variants to create;
(ii) a molecular variant population size popSize;
(iii) a crossover rate crossrate;
(iv) number of generations to create nGen;
(v) a mutation rate mutrate;
(vi) a fitness function comprising a penalty fitness function and an overall fitness function, wherein the penalty fitness is based on niche counting and the overall fitness function is based on the location of the molecular variant in a descending Pareto front divided by the shared number of molecular variants within each front; and
(vii) specific molecular variants to be automatically included in the solution set nvar; and (d) retrieving and processing the result of steps (b) and (c) with a computer microprocessor, wherein the microprocessor applies a computer program for executing the steps of:

(i) identifying a search space of acceptable molecular variants by descending from the best Pareto front backward;
(ii) generating a random population of genomes from the search space of acceptable molecular variants;
(iii) selecting a new set of genomes of size popSize from the previous population, wherein each genome consisting of nvar molecular variants is selected by applying a selection operator, a crossover operator, a mutation operator, a repair operator, and a fitness operator to the random population of genomes, and
(iv) returning the genome with the highest fitness as the final, optimized, diverse nvar set of molecular variants.

In some embodiments, the computer implemented method further comprises repeating step (iii) nGen times to select new populations of genomes of size popSize on the computer microprocessor.

6.4 IMPLEMENTATION VIA THE INTERNET

In some embodiments, the method herein can be implemented via the internet. The internet includes computers, information appliances, and computer networks that are interconnected through communication links. The interconnected computers exchange information using various services, such as electronic mail, ftp, the World Wide Web ("WWW") and other services, including secure services. The WWW service can be understood as allowing a server computer system (e.g., a Web server or a Web site) to send web pages of information to a remote client information appliance or computer system. The remote client computer system can then display the web pages. Generally, each resource (e.g., computer or web page) of the WWW is uniquely identifiable by a Uniform Resource Locator ("URL"). To view or interact with a specific web page, a client computer system specifies a URL for that web page in a request. The request is forwarded to a server that supports that web page. When the server receives the request, it sends that web page to the client information system. When the client computer system receives that web page, it can display the web page using a browser or can interact with the web page or interface as otherwise provided. A browser is a logic module that effects the requesting of web pages and displaying or interacting with web pages. Currently, displayable web pages are typically defined using a Hyper Text Markup Language ("HTML"). HTML provides a standard set of tags that define how a web page is to be displayed. An HTML document contains various tags that control the displaying of text, graphics, controls, and other features. The HTML document may contain URLs of other Web pages available on that server computer system or other server computer systems. URLs can also indicate other types of interfaces, including such things as CGI scripts or executable interfaces that information appliances use to communicate with remote information appliances or servers without necessarily displaying information to a user. In some embodiments communication over the internet is done using a wired (for example, Ethernet) network. In some embodiments communication over the internet is done using a wireless (for example, WIFI) network The internet is especially conducive to providing information services to one or more remote users or customers. In some embodiments, the methods herein can be implemented via a client-server model or system, where the server provides a user interface and the logic instruction for carrying out one or more of the various steps of the method. The server can provide an interface for entry of an objective data set of two or more properties of a plurality of molecular variants, and entry of any user definable parameters including, but not limited to the size of genomes to be selected (i.e., nvar) and the various optimization parameters, including, molecular variant population size popSize crossover rate crossrate; the number of generations to evolve nGen; the mutation rate mutrate; and the fitness function. The server also can provide a set of default values optimal under the conditions of carrying out the method (selection of molecular variants). The user or client may access the interface using a web browser and allow selection or entry of the various user definable parameters. When the user has completed selecting the items desired, the server computer system may then prompt the user for any other information needed to complete the service. The server then completes the operations needed to select the set of molecular variants. The server displays information about the completed selection back to the client computer. This transaction-specific order information may include the purchaser's name or other identification, an identification for payment (such as a corporate purchase order number or account number), or additional information needed to complete the service. Upon entry of necessary information by the client through the interface, the server provides the logic instructions for applying the method based on the parameters set by the user. The server can provide logic instructions for generating the initial Pareto front, the logic instructions for generating a random population of genomes at the server from a search space of acceptable identified by the server; and logic instructions for applying at the server a selection operator, crossover operator, mutation operator, repair operator, and fitness operator to select a first set nvar of the plurality of molecular variants. The results can be displayed as a web page, such as in the form of a HTML document, or sent via email to the client.

In some embodiments, the disclosure provides a network-based method of selecting an optimized, diverse set of molecular variants from a plurality of molecular variants, the method comprising the steps of:

(a) obtaining, at the server, a objective data set of two or more properties of a plurality of molecular variants entered at a client device;

(b) obtaining, at the server, one or more optimization parameters entered at the client device, the optimization parameters comprising:
  (i) number nvar of molecular variants to create;
  (ii) a molecular variant population size popSize;
  (iii) a crossover rate crossrate;
  (iv) a mutation rate mutrate;
  (vi) a fitness function comprising a penalty fitness function and an overall fitness function, wherein the penalty fitness is based on niche counting, and the overall fitness function is based on the location of the molecular variant in a descending Pareto front divided by the number of shared number of molecular variants; and
  (vii) specific molecular variants to be included in the nvar set of molecular variants; and (c) generating a random population of genomes at the server from a search space of acceptable molecular variants identified by the server;

(d) applying at the server a selection operator, crossover operator, mutation operator, repair operator, and fitness operator to select a first subset nvar of the plurality of molecular variants;

(e) providing the resulting first subset nvar to the client.

In some embodiments, the network includes the internet. In some embodiments, the method further comprises repeating step (d) on a combined population of the first nvar set of molecular variants and the molecular variant set popSize at the server to generate a second nvar set of molecular variants.

In some embodiments, the disclosure provides a network-based method of selecting an optimized, diverse set of molecular variants from the plurality of molecular variants, the method comprising the steps of:

(a) obtaining, at the server, a objective data set of two or more properties of a plurality of molecular variants entered at a client device;

(b) obtaining, at the server, one or more optimization parameters entered at the client device, the optimization parameters comprising:
  (i) number nvar of molecular variants to create;
  (ii) a molecular variant population size popSize;
  (iii) a crossover rate crossrate;
  (iv) number of generations to create nGen;
  (v) a mutation rate mutrate;
  (vi) a fitness function comprising a penalty fitness function and an overall fitness function, wherein the penalty fitness is based on niche counting, and the overall fitness function is based on the location of the molecular variant in a descending Pareto front divided by the shared number of molecular variants; and (vii) specific molecular variants to be included in the nvar set of molecular variants; and (c) generating a random population of genomes at the server from a search space of acceptable molecular variants identified by the server;

(d) applying at the server a selection operator, a crossover operator, a mutation operator, a repair operator, and a fitness operator to the random population of genomes; and (e) providing the resulting genome with the highest fitness as the final, optimized, diverse nvar set of molecular variants, to the client.

In some embodiments, the network includes the internet. In some embodiments, the method further comprises repeating step (d) on a combined population of the first nvar set of molecular variants and the molecular variant set popSize at the server to generate a second nvar set of molecular variants.

All publications, patents, patent applications and other documents cited in this application are hereby incorporated by reference in their entireties for all purposes to the same extent as if each individual publication, patent, patent application or other document were individually indicated to be incorporated by reference for all purposes.

While various specific embodiments have been illustrated and described, it will be appreciated that various changes can be made without departing from the spirit and scope of the invention(s).

The following Example is set forth to aid in the understanding of the invention, and is not intended and should not be construed to limit in any way the invention set forth in the claims which follow thereafter.

5. EXAMPLE

Example 1

Selecting a Panel of 96 ERED Variants from and Initial Set of 251 Variants

A set of 251 enone reductase (ERED) variants were assayed against 11 objectives and the following results were obtained:

TABLE 1

The first column of Table 1 holds the record number corresponding to an ERED variant. The remaining columns show the fold-improvement over a positive control for the conversion of the substrates Methyl Crotonate (Column 2), 2-Methyl-Cinnamonitrile (Column 3), Crotononitrile (Column 4), Et-2CN-3-Ph-2-But (Column 5), Phenyl Methacrylate (Column 6), and S-Carvone-conv (Column 7), to products.

| Col 1 | Col 2 | Col 3 | Col 4 | Col 5 | Col 6 | Col 7 |
|---|---|---|---|---|---|---|
| S02747317 | 0.33 | 0.45 | 0 | 13.21 | 5.36 | 4.32 |
| S02683110 | 0.19 | 0 | 0 | 30.04 | 1.18 | 1.58 |
| S02680809 | 0.24 | 0 | 0 | 92.67 | 1.34 | 2.64 |
| S02689522 | 0.3 | 0.93 | 0.78 | 3 | 1.29 | 0.14 |
| S02747174 | 0.28 | 0.38 | 0 | 19.43 | 1.52 | 4.3 |
| S02747414 | 0.22 | 0.52 | 0 | 14.14 | 3.56 | 4.29 |
| S02747352 | 0.39 | 0.29 | 0 | 21.15 | 3.99 | 4.27 |
| S02760534 | 0.24 | 0.3 | 0 | 6.53 | 3.06 | 4.33 |
| S02681878 | 0 | 0.59 | 0.22 | 112.32 | 17.79 | 0.47 |
| S02681023 | 0 | 0 | 0 | 51.47 | 0.78 | 2.88 |
| S02680726 | 0.3 | 0 | 0 | 47.61 | 0.75 | 0.89 |
| S02681093 | 0 | 0 | 0 | 7.47 | 0 | 2.98 |
| S02681066 | 0.32 | 0 | 0 | 9.48 | 0.45 | 2.95 |
| S02681793 | 0 | 4.06 | 0.63 | 1.31 | 40.12 | 2.92 |
| S02683173 | 0.39 | 0 | 0 | 35.93 | 0 | 1.22 |
| S02683238 | 4.02 | 0 | 0 | 9.82 | 0 | 0.13 |
| S02762203 | 0 | 0.51 | 0 | 23.42 | 0 | 0.19 |
| S02747018 | 5.49 | 0.84 | 1.62 | 6.21 | 13.55 | 3.22 |

TABLE 1-continued

The first column of Table 1 holds the record number corresponding to an ERED variant. The remaining columns show the fold-improvement over a positive control for the conversion of the substrates Methyl Crotonate (Column 2), 2-Methyl-Cinnamonitrile (Column 3), Crotononitrile (Column 4), Et-2CN-3-Ph-2-But (Column 5), Phenyl Methacrylate (Column 6), and S-Carvone-conv (Column 7), to products.

| Col 1 | Col 2 | Col 3 | Col 4 | Col 5 | Col 6 | Col 7 |
|---|---|---|---|---|---|---|
| S02683107 | 0.4 | 0 | 0 | 15.26 | 0 | 0.51 |
| S02681230 | 0.57 | 0.3 | 0 | 11.24 | 1.77 | 2.47 |
| S02681185 | 1.23 | 0.31 | 0 | 9.19 | 0.67 | 2.02 |
| S02681220 | 0.68 | 0 | 0 | 23.51 | 0.82 | 1.58 |
| S02681901 | 0 | 0.33 | 0.08 | 33.27 | 8.59 | 0.56 |
| S02683245 | 0 | 0.42 | 0 | 2.21 | 0.49 | 0.62 |
| S02760590 | 0 | 0.45 | 0 | 3.98 | 5.78 | 1.81 |
| S02761975 | 0 | 0.46 | 0 | 0.89 | 0 | 0.08 |
| S02682962 | 4.28 | 0.67 | 1.73 | 6.45 | 5.42 | 1.97 |
| S02683198 | 3.23 | 0 | 0 | 3.82 | 0 | 0.07 |
| S02681914 | 0 | 1.22 | 0.38 | 2.91 | 0.96 | 0.08 |
| S02681737 | 0 | 14.65 | 0.28 | 0.88 | 21.94 | 2.38 |
| S02760822 | 0.26 | 9.27 | 0.33 | 3.98 | 35.56 | 3.84 |
| S02683189 | 0.28 | 0.39 | 0 | 5.84 | 0.64 | 1.39 |
| S02760925 | 0.24 | 9.18 | 0.35 | 1.45 | 34.08 | 3.57 |
| S02681817 | 0.29 | 0.62 | 0.65 | 19.97 | 5.1 | 0.23 |
| S02682981 | 4.35 | 0.41 | 0.95 | 6.93 | 4.38 | 2.95 |
| S02680953 | 0.83 | 0 | 0 | 2.12 | 0.84 | 1.36 |
| S02680872 | 4.15 | 0.59 | 1.42 | 5.15 | 4.37 | 1.69 |
| S02760924 | 0.1 | 4.8 | 0.13 | 1.88 | 32.55 | 3.93 |
| S02761906 | 0 | 0.44 | 0 | 5.11 | 21.22 | 0.9 |
| S02679642 | 1.16 | 1.8 | 1.44 | 2.32 | 3.56 | 0.43 |
| S02681855 | 0.25 | 0.28 | 0.56 | 6.37 | 2.36 | 0.27 |
| S02777151 | 0 | 0.53 | 0.22 | 23.55 | 4.09 | 0.19 |
| S02760913 | 0 | 8.29 | 0.25 | 0.97 | 30.49 | 3.51 |
| S02681879 | 0 | 0.82 | 0 | 15.62 | 26.26 | 0.4 |
| S02689546 | 0.41 | 0.52 | 0.73 | 5.33 | 1.55 | 0.16 |
| S02681426 | 0 | 11.21 | 0.3 | 1.08 | 20.78 | 2.52 |
| S02760937 | 0.29 | 7.99 | 0.27 | 1.31 | 26.05 | 3.58 |
| S02681730 | 0 | 6.62 | 0.28 | 0.9 | 33.09 | 2.19 |
| S02693241 | 0.27 | 0.48 | 0.11 | 1.32 | 0.42 | 0.67 |
| S02679726 | 1.11 | 0.78 | 1.54 | 2.4 | 4.4 | 0.85 |
| S02679574 | 1.02 | 0.98 | 1.54 | 2.02 | 4.98 | 1.29 |
| S02681670 | 0 | 0.29 | 0.15 | 3.98 | 6.39 | 0.62 |
| S02689613 | 0 | 0.68 | 0.29 | 4.52 | 5.07 | 0.35 |
| S02762127 | 0 | 0.43 | 0 | 4.74 | 0 | 0.07 |
| S02681796 | 0 | 2.18 | 0.24 | 1.42 | 24.02 | 1.41 |
| S02760961 | 0 | 6.76 | 0.19 | 0.92 | 24.42 | 2.79 |
| S02681531 | 0 | 4.18 | 0.2 | 1.42 | 33.32 | 1.61 |
| S02762167 | 0.17 | 8.81 | 0.21 | 8.76 | 19.9 | 2.91 |
| S02681828 | 0 | 0.55 | 0 | 10.62 | 4.28 | 0.42 |
| S02681487 | 0 | 2.66 | 0.19 | 2.09 | 1.89 | 1.32 |
| S02678915 | 0 | 9.25 | 0.36 | 0.82 | 20.33 | 2.41 |
| S02679497 | 0.37 | 0.3 | 1.22 | 1.31 | 0.38 | 1.91 |
| S02777077 | 0.13 | 8.51 | 0.14 | 1.72 | 14.77 | 3 |
| S02678918 | 0 | 8.8 | 0.34 | 0.81 | 20.4 | 2.69 |
| S02682781 | 0.49 | 1.09 | 0.43 | 6.56 | 5.89 | 1.92 |
| S02761717 | 0 | 0.78 | 0 | 2.82 | 23 | 2.01 |
| S02681774 | 0 | 0.95 | 0.28 | 29.04 | 18.91 | 1.02 |
| S02777053 | 0 | 8.3 | 0.13 | 1.4 | 11.55 | 1.82 |
| S02681474 | 0 | 1.88 | 0.12 | 1.36 | 13.56 | 1.44 |
| S02777496 | 0.19 | 4.2 | 0.34 | 1.81 | 23.98 | 2.93 |
| S02679696 | 0.88 | 1.19 | 1.38 | 3.38 | 5.8 | 1.12 |
| S02761627 | 0 | 3.12 | 0.21 | 3.32 | 22.09 | 2.89 |
| S02681340 | 0.24 | 0.55 | 0.51 | 4.68 | 1.89 | 1.91 |
| S02777369 | 0 | 0.88 | 0 | 1.76 | 21.67 | 1.89 |
| S02761978 | 0 | 1.51 | 0.24 | 9.44 | 23.18 | 2.79 |
| S02678954 | 0.13 | 6.08 | 0.4 | 1.59 | 7.43 | 2.6 |
| S02762113 | 0 | 0.42 | 0 | 4.33 | 20.75 | 2.2 |
| S02761830 | 0.15 | 0.56 | 0.45 | 64.46 | 8.74 | 2.15 |
| S02746981 | 2.5 | 0.86 | 0.9 | 11.3 | 9.08 | 2.74 |
| S02679477 | 0.29 | 0.38 | 1.27 | 1.5 | 1.23 | 1.82 |
| S02679117 | 0.77 | 1.06 | 1.3 | 1.06 | 15.45 | 1.17 |
| S02679624 | 1.16 | 1.04 | 1.15 | 1.46 | 2.79 | 0.9 |
| S02678987 | 0 | 7.94 | 0.34 | 0.81 | 13.6 | 2.62 |
| S02681285 | 0 | 1.16 | 0.14 | 1.31 | 9.87 | 1.12 |
| S02681451 | 0 | 6.62 | 0.1 | 1.02 | 16.27 | 1.67 |
| S02777051 | 0.33 | 2.68 | 0.23 | 0.8 | 7.28 | 2.14 |
| S02679586 | 1.04 | 0.64 | 0.85 | 2.48 | 1.75 | 1.17 |
| S02762123 | 0 | 0.81 | 0.08 | 2.74 | 20.19 | 1.65 |
| S02680836 | 1.17 | 0.37 | 0.8 | 13.38 | 7 | 0.77 |

TABLE 1-continued

The first column of Table 1 holds the record number corresponding to an ERED variant. The remaining columns show the fold-improvement over a positive control for the conversion of the substrates Methyl Crotonate (Column 2), 2-Methyl-Cinnamonitrile (Column 3), Crotononitrile (Column 4), Et-2CN-3-Ph-2-But (Column 5), Phenyl Methacrylate (Column 6), and S-Carvone-conv (Column 7), to products.

| Col 1 | Col 2 | Col 3 | Col 4 | Col 5 | Col 6 | Col 7 |
|---|---|---|---|---|---|---|
| S02777001 | 1.24 | 0.5 | 0 | 16.06 | 1.03 | 0.31 |
| S02679646 | 1.32 | 0.86 | 1.08 | 3.95 | 3.26 | 1.33 |
| S02681662 | 0 | 0.86 | 0.13 | 1.79 | 14.01 | 0.07 |
| S02679037 | 0 | 5.61 | 0.17 | 1.08 | 14.59 | 2.67 |
| S02761651 | 0.11 | 0 | 0 | 2.64 | 16.28 | 1.25 |
| S02681527 | 0 | 0.73 | 0.96 | 0.75 | 5.05 | 0.27 |
| S02681038 | 0.44 | 0.31 | 0.3 | 49.94 | 1.46 | 1.82 |
| S02683135 | 0 | 0.38 | 0 | 16.49 | 2.82 | 1.39 |
| S02762008 | 0 | 0.89 | 0 | 3.16 | 11.54 | 2.8 |
| S02683108 | 0 | 0.38 | 0 | 8.22 | 3.6 | 1.75 |
| S02683154 | 0.88 | 0.49 | 0 | 8.27 | 4.72 | 1.64 |
| S02682933 | 0.98 | 0.52 | 1.04 | 0.88 | 0.39 | 0.65 |
| S02777468 | 0 | 1 | 0.07 | 3.65 | 11.05 | 2.65 |
| S02679402 | 0.99 | 0 | 0.08 | 36.67 | 4.2 | 2.51 |
| S02679281 | 0 | 4.33 | 0.5 | 5.67 | 20.17 | 2.45 |
| S02680778 | 2.18 | 0.44 | 0.86 | 3.58 | 1.82 | 1.12 |
| S02679570 | 1.07 | 0 | 0.22 | 6.54 | 14.55 | 2.99 |
| S02679399 | 1.2 | 1.13 | 1.12 | 2.05 | 2.99 | 1.36 |
| S02681490 | 0 | 1.5 | 0.08 | 3.29 | 2.95 | 2.05 |
| S02682810 | 0.99 | 0.93 | 0.86 | 0.88 | 0.98 | 0.46 |
| S02681836 | 0 | 1.05 | 0.19 | 19.7 | 0.61 | 2.13 |
| S02761025 | 0 | 1.05 | 0.14 | 2.59 | 10.27 | 2.81 |
| S02681080 | 0.36 | 0 | 0.3 | 0.92 | 0.49 | 0.38 |
| S02761075 | 0.21 | 1.28 | 0.28 | 2.89 | 10.23 | 2.69 |
| S02679376 | 1.78 | 1.33 | 0.96 | 3.6 | 5.35 | 1.66 |
| S02681238 | 1.02 | 0 | 0.3 | 1.75 | 1.02 | 0.58 |
| S02682790 | 1.05 | 0.9 | 0.83 | 0.8 | 1.46 | 0.46 |
| S02679510 | 0.58 | 0.26 | 0.43 | 3.06 | 1.79 | 2.64 |
| S02777061 | 0.27 | 2.09 | 0.13 | 1.1 | 3.04 | 1.4 |
| S02679287 | 1.01 | 1.36 | 1.04 | 2.16 | 3.53 | 1.29 |
| S02683061 | 1.95 | 0.66 | 0.6 | 6.58 | 8.83 | 2.35 |
| S02681664 | 0.21 | 0.67 | 0.64 | 2.84 | 4.34 | 1.7 |
| S02680675 | 0.67 | 0.68 | 0.71 | 1.11 | 0.49 | 0.51 |
| S02761741 | 0.25 | 0.98 | 0.2 | 0.9 | 3.16 | 2.5 |
| S02761744 | 0.39 | 0.46 | 0.39 | 16.13 | 8.07 | 1.35 |
| S02679296 | 0.21 | 1.08 | 0.38 | 14.36 | 6.76 | 2.37 |
| S02680858 | 0.66 | 0.72 | 0.75 | 1.88 | 0.58 | 0.6 |
| S02777462 | 0.3 | 2.19 | 0.14 | 4.09 | 3.38 | 1.42 |
| S02761985 | 0 | 0.82 | 0.28 | 3.17 | 10.36 | 2.58 |
| S02693300 | 1.12 | 1.5 | 0.83 | 6.66 | 11.24 | 2.22 |
| S02679508 | 0 | 0.49 | 0.76 | 10.47 | 4.71 | 2.26 |
| S02681148 | 0.74 | 0.59 | 0.56 | 1.67 | 0.64 | 0.68 |
| S02679550 | 0 | 0.5 | 0.72 | 11.42 | 2.5 | 2.19 |
| S02679720 | 0.66 | 0.77 | 0.81 | 2.27 | 6.76 | 0.65 |
| S02681213 | 0.85 | 0 | 0.29 | 2.28 | 1.04 | 1.22 |
| S02679373 | 0.76 | 1.26 | 0.84 | 1.05 | 1.61 | 1.38 |
| S02679631 | 0.57 | 0.6 | 0.68 | 1.89 | 5.24 | 0.53 |
| S02762197 | 0.54 | 0.63 | 0.24 | 28.19 | 7.15 | 2.2 |
| S02682894 | 0 | 0.4 | 0.53 | 2.81 | 1.54 | 1.05 |
| S02762065 | 0.33 | 0.64 | 0.28 | 28.28 | 10.74 | 1.65 |
| S02681896 | 0.52 | 0.85 | 0.7 | 5.27 | 4.65 | 0.99 |
| S02681328 | 0.45 | 1.81 | 0.52 | 1.95 | 4.8 | 0.88 |
| S02679454 | 0 | 0.75 | 0.36 | 9.41 | 2.47 | 2.04 |
| S02679244 | 0.11 | 1.3 | 0.43 | 6.75 | 9 | 2.37 |
| S02680620 | 0.38 | 1.04 | 0.68 | 3.23 | 3.98 | 1.75 |
| S02679350 | 0.53 | 1.34 | 0.57 | 12.36 | 4.95 | 1.85 |
| S02679605 | 0.18 | 0.61 | 0.45 | 5.28 | 10.51 | 1.26 |
| S02679560 | 0.27 | 1.04 | 0.52 | 8.46 | 5.12 | 1.51 |
| S02681057 | 0 | 0 | 0 | 2.99 | 0.37 | 3.07 |
| S02680926 | 0 | 0 | 0 | 30.49 | 0.36 | 2.84 |
| S02681104 | 0.1 | 0 | 0 | 6.42 | 2.13 | 3.09 |
| S02680945 | 0.11 | 0 | 0 | 15.41 | 2.03 | 3.06 |
| S02683156 | 0.2 | 0 | 0 | 50.39 | 1.05 | 0.89 |
| S02681144 | 0 | 0 | 0 | 23.72 | 0.46 | 2.17 |
| S02760353 | 0 | 0.31 | 0 | 1.34 | 0 | 0.54 |
| S02683122 | 0.16 | 0 | 0 | 20.64 | 0.34 | 0.76 |
| S02680796 | 0.12 | 0 | 0 | 3.26 | 0.78 | 1.69 |
| S02682978 | 4.39 | 0 | 1.23 | 5.4 | 5.11 | 1.59 |
| S02682979 | 4.24 | 0.53 | 0.98 | 1.31 | 4.28 | 2.08 |
| S02681028 | 0 | 0 | 0 | 1.15 | 0.54 | 1.86 |
| S02683246 | 0.49 | 0 | 0 | 9.15 | 0 | 0.07 |
| S02681632 | 0 | 3.53 | 0.55 | 0.8 | 19.88 | 2.08 |
| S02681754 | 0 | 0.72 | 0.06 | 0.81 | 4.76 | 0.61 |
| S02760453 | 0 | 0.26 | 0 | 4.84 | 0 | 0.09 |
| S02761657 | 0 | 7.86 | 0.11 | 0.79 | 14.09 | 2.6 |
| S02761593 | 0 | 2.74 | 0.1 | 1.97 | 21.99 | 2.64 |
| S02680933 | 0.13 | 0 | 0 | 4.52 | 0.33 | 1.08 |
| S02680598 | 0 | 0 | 0 | 5.99 | 1.39 | 1.43 |
| S02681345 | 0 | 2.1 | 0 | 1.22 | 20.02 | 1.7 |
| S02777015 | 0 | 7.26 | 0 | 0.72 | 10.83 | 2.33 |
| S02681534 | 0 | 0 | 0.17 | 2.05 | 0.23 | 0.06 |
| S02678906 | 0 | 9.24 | 0.2 | 0.72 | 11.5 | 2.39 |
| S02761583 | 0 | 0.48 | 0.09 | 44.56 | 8.63 | 0.2 |
| S02777420 | 0 | 0.44 | 0 | 0.64 | 0 | 0.05 |
| S02683120 | 0 | 0 | 0 | 12.17 | 0.54 | 0.93 |
| S02760983 | 0 | 1.35 | 0 | 2.39 | 25.87 | 0.2 |
| S02762229 | 0 | 0.55 | 0 | 2.86 | 5.74 | 0.18 |
| S02777327 | 0 | 0.74 | 0 | 2.23 | 2.56 | 2.3 |
| S02682782 | 1.1 | 0.74 | 0.68 | 1.15 | 1.73 | 0.69 |
| S02681470 | 0.25 | 0.38 | 0.46 | 3.15 | 0.6 | 0.16 |
| S02681254 | 0 | 0 | 0.08 | 15.87 | 2.98 | 0.38 |
| S02681701 | 0 | 1.51 | 0.23 | 1.1 | 16.08 | 0.34 |
| S02680988 | 2.43 | 0.47 | 0.77 | 5.92 | 4.64 | 1.28 |
| S02679122 | 0.12 | 1.1 | 0.3 | 0.86 | 20.16 | 1.18 |
| S02762134 | 0.14 | 0.42 | 0.11 | 13.7 | 0.23 | 0.07 |
| S02761824 | 0 | 0.81 | 0 | 1.54 | 17.13 | 1.85 |
| S02681181 | 0.98 | 0.46 | 0.56 | 4.3 | 4.83 | 1.04 |
| S02693243 | 0 | 0.42 | 0.1 | 1.74 | 0.63 | 1.02 |
| S02761563 | 0 | 1.02 | 0 | 3.28 | 11.66 | 2.46 |
| S02683055 | 2.64 | 0.65 | 0.69 | 2.21 | 1.58 | 1.12 |
| S02760954 | 0 | 1.17 | 0.13 | 6.45 | 13.12 | 0.53 |
| S02681857 | 0 | 0.66 | 0 | 0.95 | 2.88 | 0.63 |
| S02681715 | 0 | 4.73 | 0 | 1.04 | 4.25 | 0.41 |
| S02683164 | 2.22 | 0.74 | 0.23 | 4.92 | 0.5 | 0.64 |
| S02693285 | 0.33 | 0.7 | 0.2 | 2.21 | 0.85 | 1.53 |
| S02681877 | 0 | 0.38 | 0 | 2.33 | 11.92 | 0.06 |
| S02681516 | 0 | 0.7 | 0.3 | 13.32 | 5.98 | 0.85 |
| S02679236 | 0.34 | 0.73 | 0.37 | 0.68 | 0.41 | 0.85 |
| S02681529 | 0 | 0.48 | 0.21 | 3.15 | 9.5 | 2.2 |
| S02683015 | 1.57 | 0.38 | 0.44 | 1.13 | 1.8 | 1 |
| S02681822 | 0 | 0 | 0 | 17.5 | 1.66 | 0.31 |
| S02683023 | 1.55 | 0.36 | 0.48 | 2.16 | 1.91 | 0.87 |
| S02762060 | 0.36 | 0.48 | 0.3 | 0.82 | 0.66 | 0.1 |
| S02681288 | 0 | 1.43 | 0 | 2.43 | 1.92 | 0.16 |
| S02679516 | 0.35 | 0.4 | 0.5 | 1.34 | 1.35 | 0.4 |
| S02681011 | 0.57 | 0.44 | 0.59 | 1.03 | 0.71 | 0.78 |
| S02679127 | 0.8 | 0.95 | 0.42 | 0.84 | 1.04 | 0.34 |
| S02679614 | 0.21 | 0.3 | 0.2 | 0.99 | 2.36 | 0.57 |
| S02679734 | 0.58 | 0.94 | 0.38 | 0.62 | 0.46 | 0.76 |
| S02680909 | 0.43 | 0 | 0.33 | 1.22 | 0.78 | 0.47 |
| S02683105 | 0 | 0 | 0 | 22.1 | 0 | 0.14 |
| S02680839 | 0 | 0 | 0 | 0.6 | 0 | 0.06 |
| S02681102 | 0 | 0 | 0 | 4.08 | 0.36 | 0.9 |
| S02681264 | 0 | 0.29 | 0.21 | 2.01 | 0.12 | 0.06 |
| S02683035 | 2.31 | 0.38 | 0.45 | 1.77 | 1.07 | 1.09 |
| S02681129 | 0 | 1.62 | 0.07 | 0.93 | 15.69 | 2.1 |
| S02681689 | 0 | 0.28 | 0.16 | 1.32 | 0.19 | 0.08 |
| S02681475 | 0 | 0 | 0 | 2.64 | 1.65 | 0.21 |
| S02680984 | 0.74 | 0.33 | 0.51 | 2.2 | 1.2 | 0.73 |
| S02682855 | 0.36 | 0.64 | 0.33 | 0.68 | 0.41 | 0.2 |
| S02681708 | 0 | 0.52 | 0.1 | 0.46 | 14.32 | 0.17 |
| S02762013 | 0 | 0.51 | 0 | 1.07 | 2.25 | 0.06 |
| S02761566 | 0 | 0.46 | 0 | 0.68 | 0 | 0.04 |
| S02680910 | 0.2 | 0 | 0.2 | 1.72 | 0.44 | 0.46 |
| S02681709 | 0 | 0.54 | 0 | 0.72 | 2.56 | 0.22 |
| S02689527 | 0 | 0 | 0.39 | 1.52 | 3.34 | 0.2 |
| S02761611 | 0 | 0.36 | 0 | 0.92 | 0 | 0.04 |
| S02681741 | 0 | 0.31 | 0 | 2.79 | 1.25 | 0.33 |
| S02761580 | 0 | 0.43 | 0 | 0.6 | 1.91 | 0.21 |
| S02761635 | 0 | 0.43 | 0 | 0.91 | 0 | 0.05 |
| S02693315 | 0 | 0.3 | 0 | 0.63 | 0 | 0.07 |
| S02760951 | 0 | 1.12 | 0 | 0.66 | 4.74 | 0.1 |

TABLE 1-continued

The first column of Table 1 holds the record number corresponding to an ERED variant. The remaining columns show the fold-improvement over a positive control for the conversion of the substrates Methyl Crotonate (Column 2), 2-Methyl-Cinnamonitrile (Column 3), Crotononitrile (Column 4), Et-2CN-3-Ph-2-But (Column 5), Phenyl Methacrylate (Column 6), and S-Carvone-conv (Column 7), to products.

| Col 1 | Col 2 | Col 3 | Col 4 | Col 5 | Col 6 | Col 7 |
|---|---|---|---|---|---|---|
| S02681101 | 0 | 0 | 0.09 | 0.94 | 0.7 | 0.62 |
| S02777203 | 0 | 0.9 | 0 | 1.1 | 13.32 | 0.23 |
| S02777086 | 0 | 0.77 | 0 | 0.85 | 12.33 | 0.34 |
| S02678934 | 0 | 0.54 | 0 | 0.58 | 0 | 0.13 |
| S02681463 | 0 | 0.41 | 0 | 0.99 | 4.64 | 0.16 |
| S02760943 | 0 | 1.99 | 0 | 0.74 | 7.46 | 0.18 |
| S02681851 | 0 | 0.35 | 0 | 1.01 | 5.97 | 0.15 |
| S02679504 | 0 | 0 | 0.09 | 0.81 | 0 | 0.12 |
| S02776856 | 0 | 1.55 | 0 | 0.73 | 4.07 | 0.18 |
| S02681889 | 0 | 0.66 | 0 | 1.34 | 5.05 | 0.1 |
| S02681924 | 0 | 0.39 | 0 | 0.82 | 3.11 | 0.3 |
| S02683143 | 0 | 0 | 0 | 0.76 | 0 | 0.04 |
| S02760958 | 0 | 1.49 | 0 | 0.56 | 10.04 | 0.3 |
| S02681811 | 0 | 0 | 0 | 1.08 | 0 | 0.03 |
| S02761104 | 0 | 1.59 | 0 | 0.74 | 2.13 | 0.11 |
| S02761644 | 0 | 0.48 | 0 | 0.67 | 0 | 0.03 |
| S02761602 | 0 | 0.39 | 0 | 0.76 | 0 | 0.04 |
| S02762215 | 0 | 0.45 | 0 | 0.45 | 0 | 0.08 |
| S02693267 | 0 | 0.35 | 0 | 0.65 | 0 | 0.09 |
| S02693321 | 0 | 0.41 | 0 | 0.67 | 0 | 0.07 |

TABLE 2

This Table continues presenting the initial ERED variants used for the selection. The first column of Table 2 holds the record number corresponding to an ERED variant. The remaining columns show the fold-improvement over a positive control for the conversion of the substrates Dione_R (Column 8), Dione_S (Column 9), Dione-conv (Column 10), S-carvone_R (Column 11), and S-carvone_S (Column 12), to products.

| Col 1 | Col 8 | Col 9 | Col 10 | Col 11 | Col 12 |
|---|---|---|---|---|---|
| S02747317 | 14.92 | 0 | 0.24 | 0 | 99.34 |
| S02683110 | 0 | 3.04 | 0.22 | 0 | 100 |
| S02680809 | 100 | 0 | 0.87 | 0 | 98.54 |
| S02689522 | 0 | 72.99 | 1.98 | 22.53 | 0 |
| S02747174 | 100 | 0 | 0.19 | 0 | 100 |
| S02747414 | 100 | 0 | 0.15 | 0 | 100 |
| S02747352 | 100 | 0 | 0.33 | 0 | 100 |
| S02760534 | 100 | 0 | 0.17 | 0 | 93.5 |
| S02681878 | 0 | 33.4 | 1.2 | 68.9 | 0 |
| S02681023 | 100 | 0 | 0.52 | 0 | 100 |
| S02680726 | 100 | 0 | 0.64 | 0 | 95.54 |
| S02681093 | 100 | 0 | 0.35 | 0 | 99.39 |
| S02681066 | 100 | 0 | 0.47 | 0 | 98.82 |
| S02681793 | 98.72 | 0 | 12.41 | 94.67 | 0 |
| S02683173 | 100 | 0 | 0.11 | 0 | 96.48 |
| S02683238 | 100 | 0 | 0.21 | 0 | 0.83 |
| S02762203 | 0 | 0 | 0.52 | 0 | 59.11 |
| S02747018 | 50.29 | 0 | 0.97 | 91.9 | 0 |
| S02683107 | 100 | 0 | 0.14 | 0 | 89.38 |
| S02681230 | 100 | 0 | 0.13 | 0 | 91.2 |
| S02681185 | 100 | 0 | 0.19 | 0 | 84.33 |
| S02681220 | 100 | 0 | 0.19 | 0 | 65.88 |
| S02681901 | 0 | 53.35 | 2.08 | 58.17 | 0 |
| S02683245 | 100 | 0 | 0.23 | 0 | 53.32 |
| S02760590 | 100 | 0 | 0.13 | 0 | 64.3 |
| S02761975 | 100 | 0 | 0.37 | 0 | 34.72 |
| S02682962 | 55.61 | 0 | 0.62 | 92.68 | 0 |
| S02683198 | 100 | 0 | 0.49 | 21.52 | 0 |
| S02681914 | 0 | 37.24 | 0.88 | 32.4 | 0 |
| S02681737 | 93 | 0 | 1.16 | 93.82 | 0 |
| S02760822 | 95.82 | 0 | 2.09 | 92.49 | 0 |
| S02683189 | 100 | 0 | 0.14 | 0 | 47.48 |
| S02760925 | 100 | 0 | 0.75 | 92.9 | 0 |
| S02681817 | 0 | 46.36 | 0.9 | 66.65 | 0 |
| S02682981 | 22.42 | 0 | 0.74 | 90.76 | 0 |
| S02680953 | 100 | 0 | 0.17 | 6.03 | 0 |
| S02680872 | 52.92 | 0 | 0.65 | 88.22 | 0 |
| S02760924 | 97.1 | 0 | 1.98 | 92.12 | 0 |
| S02761906 | 100 | 0 | 0.14 | 16.07 | 0 |
| S02679642 | 0 | 1.7 | 2.1 | 78.65 | 0 |
| S02681855 | 0 | 34.78 | 3.14 | 57.48 | 0 |
| S02777151 | 0 | 16.22 | 0.74 | 44.94 | 0 |
| S02760913 | 73.19 | 0 | 0.79 | 94.25 | 0 |
| S02681879 | 8.34 | 0 | 1.27 | 74.3 | 0 |
| S02689546 | 0 | 26.97 | 1.04 | 62.72 | 0 |
| S02681426 | 94.1 | 0 | 1.11 | 93.8 | 0 |
| S02760937 | 87.03 | 0 | 0.74 | 92.12 | 0 |
| S02681730 | 95.03 | 0 | 1.96 | 93.16 | 0 |
| S02693241 | 0 | 16.7 | 2.57 | 86.67 | 0 |
| S02679726 | 28.05 | 0 | 1.44 | 80.69 | 0 |
| S02679574 | 24.93 | 0 | 1.68 | 84.2 | 0 |
| S02681670 | 0 | 0.87 | 0.96 | 60.2 | 0 |
| S02689613 | 0 | 6.25 | 0.97 | 61.24 | 0 |
| S02762127 | 100 | 0 | 0.8 | 46.62 | 0 |
| S02681796 | 96.01 | 0 | 7.45 | 91.12 | 0 |
| S02760961 | 100 | 0 | 0.44 | 93.85 | 0 |
| S02681531 | 71.66 | 0 | 3.69 | 91.73 | 0 |
| S02762167 | 89.86 | 0 | 0.68 | 91.62 | 0 |
| S02681828 | 8.74 | 0 | 3.18 | 80.29 | 0 |
| S02681487 | 25.6 | 0 | 7.65 | 91.39 | 0 |
| S02678915 | 92.18 | 0 | 0.79 | 90.58 | 0 |
| S02679497 | 19.36 | 0 | 0.51 | 92.95 | 0 |
| S02777077 | 91.11 | 0 | 2.96 | 91.38 | 0 |
| S02678918 | 87.68 | 0 | 0.92 | 90.72 | 0 |
| S02682781 | 0 | 0 | 0 | 90.45 | 0 |
| S02761717 | 95.88 | 0 | 5.78 | 88.35 | 0 |
| S02681774 | 12.86 | 0 | 1.39 | 67.8 | 0 |
| S02777053 | 100 | 0 | 0.42 | 93 | 0 |
| S02681474 | 95.4 | 0 | 7.74 | 88.99 | 0 |
| S02777496 | 100 | 0 | 1.32 | 91.44 | 0 |
| S02679696 | 32.78 | 0 | 1.43 | 79.12 | 0 |
| S02761627 | 100 | 0 | 0.83 | 91.12 | 0 |
| S02681340 | 7.25 | 0 | 2.8 | 89.17 | 0 |
| S02777369 | 93.55 | 0 | 5.18 | 87.81 | 0 |
| S02761978 | 92.73 | 0 | 4 | 94.21 | 0 |
| S02678954 | 78.81 | 0 | 6.44 | 91.2 | 0 |
| S02762113 | 100 | 0 | 1.36 | 89.96 | 0 |
| S02761830 | 60.27 | 0 | 1.02 | 77.36 | 0 |
| S02746981 | 48.88 | 0 | 1.16 | 87.98 | 0 |
| S02679477 | 50.34 | 0 | 0.92 | 93.2 | 0 |
| S02679117 | 57.25 | 0 | 2.07 | 84.09 | 0 |
| S02679624 | 30.7 | 0 | 1.45 | 87.25 | 0 |
| S02678987 | 82.45 | 0 | 1.36 | 93.02 | 0 |
| S02681285 | 96.67 | 0 | 6.14 | 85.71 | 0 |
| S02681451 | 95.99 | 0 | 1.73 | 91.3 | 0 |
| S02777051 | 25.92 | 0 | 5.54 | 92.75 | 0 |
| S02679586 | 17.44 | 0 | 1.08 | 89.63 | 0 |
| S02762123 | 80.6 | 0 | 5.83 | 87.49 | 0 |
| S02680836 | 17.81 | 0 | 1.06 | 80.38 | 0 |
| S02777001 | 40.53 | 0 | 1.11 | 76.54 | 0 |
| S02679646 | 26.73 | 0 | 1.72 | 87.77 | 0 |
| S02681662 | 66.31 | 0 | 4.34 | 63.78 | 0 |
| S02679037 | 96.22 | 0 | 2.58 | 89.67 | 0 |
| S02761651 | 100 | 0 | 0.82 | 82.08 | 0 |
| S02681527 | 79.88 | 0 | 0.99 | 83.72 | 0 |
| S02681038 | 73.49 | 0 | 0.23 | 90.73 | 0 |
| S02683135 | 100 | 0 | 0.3 | 74.32 | 0 |
| S02762008 | 87.81 | 0 | 3.91 | 90.43 | 0 |
| S02683108 | 100 | 0 | 0.16 | 79.07 | 0 |
| S02683154 | 100 | 0 | 0.13 | 78.77 | 0 |
| S02682933 | 65.17 | 0 | 0.8 | 87.5 | 0 |
| S02777468 | 90.11 | 0 | 4.14 | 90.4 | 0 |
| S02679402 | 63.78 | 0 | 0.33 | 86.86 | 0 |
| S02679281 | 87.18 | 0 | 3.27 | 87.35 | 0 |
| S02680778 | 64.65 | 0 | 0.75 | 88.77 | 0 |

TABLE 2-continued

This Table continues presenting the initial ERED variants used for the selection. The first column of Table 2 holds the record number corresponding to an ERED variant. The remaining columns show the fold-improvement over a positive control for the conversion of the substrates Dione_R (Column 8), Dione_S (Column 9), Dione-conv (Column 10), S-carvone_R (Column 11), and S-carvone_S (Column 12), to products.

| Col 1 | Col 8 | Col 9 | Col 10 | Col 11 | Col 12 |
|---|---|---|---|---|---|
| S02679570 | 68.46 | 0 | 0.38 | 90.45 | 0 |
| S02679399 | 70 | 0 | 2.18 | 77.66 | 0 |
| S02681490 | 77.31 | 0 | 5.16 | 89.58 | 0 |
| S02682810 | 46.89 | 0 | 0.73 | 80.84 | 0 |
| S02681836 | 42.98 | 0 | 0.56 | 93.35 | 0 |
| S02761025 | 47.67 | 0 | 2.71 | 92.13 | 0 |
| S02681080 | 74.01 | 0 | 0.38 | 75.5 | 0 |
| S02761075 | 90.72 | 0 | 3.12 | 93.86 | 0 |
| S02679376 | 46.02 | 0 | 2.6 | 80.16 | 0 |
| S02681238 | 69.92 | 0 | 0.42 | 91.32 | 0 |
| S02682790 | 58.64 | 0 | 0.92 | 79.49 | 0 |
| S02679510 | 49.65 | 0 | 0.82 | 94 | 0 |
| S02777061 | 92.28 | 0 | 2.01 | 87.5 | 0 |
| S02679287 | 47.47 | 0 | 1.68 | 78.36 | 0 |
| S02683061 | 58.44 | 0 | 0.97 | 90.98 | 0 |
| S02681664 | 29.47 | 0 | 2.62 | 84.74 | 0 |
| S02680675 | 50.84 | 0 | 1.03 | 82.84 | 0 |
| S02761741 | 79.63 | 0 | 2.42 | 91.96 | 0 |
| S02761744 | 29.77 | 0 | 1.8 | 85.06 | 0 |
| S02679296 | 36.37 | 0 | 2.86 | 83.03 | 0 |
| S02680858 | 57.14 | 0 | 0.97 | 77.71 | 0 |
| S02777462 | 86.02 | 0 | 2.16 | 87.1 | 0 |
| S02761985 | 78.76 | 0 | 2.16 | 91.19 | 0 |
| S02693300 | 49.41 | 0 | 2.11 | 80.28 | 0 |
| S02679508 | 59.22 | 0 | 1.11 | 91.3 | 0 |
| S02681148 | 59.9 | 0 | 0.48 | 78.17 | 0 |
| S02679550 | 57.17 | 0 | 1.2 | 89.12 | 0 |
| S02679720 | 55.84 | 0 | 1.64 | 77.43 | 0 |
| S02681213 | 68.35 | 0 | 0.64 | 88.31 | 0 |
| S02679373 | 57.26 | 0 | 1.06 | 86.94 | 0 |
| S02679631 | 60.07 | 0 | 1.44 | 81.43 | 0 |
| S02762197 | 65.07 | 0 | 1.28 | 86.73 | 0 |
| S02682894 | 67.62 | 0 | 1.31 | 77.53 | 0 |
| S02762065 | 59.72 | 0 | 1.6 | 84.31 | 0 |
| S02681896 | 62.5 | 0 | 1.9 | 89.61 | 0 |
| S02681328 | 71.68 | 0 | 2.22 | 83.83 | 0 |
| S02679454 | 64.44 | 0 | 1.76 | 82.21 | 0 |
| S02679244 | 63.64 | 0 | 2.69 | 80.44 | 0 |
| S02680620 | 61.16 | 0 | 1.59 | 79.92 | 0 |
| S02679350 | 51.78 | 0 | 2.32 | 79.76 | 0 |
| S02679605 | 56.58 | 0 | 1.76 | 74.88 | 0 |
| S02679560 | 68.89 | 0 | 1.74 | 70.26 | 0 |
| S02681057 | 100 | 0 | 0.22 | 0 | 100 |
| S02680926 | 100 | 0 | 0.16 | 0 | 100 |
| S02681104 | 100 | 0 | 0.14 | 0 | 100 |
| S02680945 | 100 | 0 | 0.18 | 0 | 100 |
| S02683156 | 100 | 0 | 0.11 | 0 | 93.86 |
| S02681144 | 100 | 0 | 0.34 | 0 | 98.67 |
| S02760353 | 100 | 0 | 0.14 | 0 | 94.87 |
| S02683122 | 100 | 0 | 0.62 | 0 | 94.84 |
| S02680796 | 100 | 0 | 0.2 | 0 | 82.51 |
| S02682978 | 48.86 | 0 | 0.61 | 91.68 | 0 |
| S02682979 | 15.22 | 0 | 0.51 | 90.31 | 0 |
| S02681028 | 86.51 | 0 | 0.51 | 0 | 79.84 |
| S02683246 | 100 | 0 | 0.16 | 0 | 64.12 |
| S02681632 | 87.84 | 0 | 8.29 | 93.8 | 0 |
| S02681754 | 96.57 | 0 | 9.93 | 80.06 | 0 |
| S02760453 | 100 | 0 | 0.16 | 4.12 | 0 |
| S02761657 | 92.91 | 0 | 0.87 | 90.81 | 0 |
| S02761593 | 100 | 0 | 0.76 | 90.44 | 0 |
| S02680933 | 100 | 0 | 0.4 | 0 | 35.28 |
| S02680598 | 100 | 0 | 0.22 | 0 | 21.62 |
| S02681345 | 94.35 | 0 | 6.82 | 83.91 | 0 |
| S02777015 | 100 | 0 | 0.63 | 90.02 | 0 |
| S02681534 | 0 | 34.92 | 0.8 | 59.14 | 0 |
| S02678906 | 66.88 | 0 | 0.75 | 91.28 | 0 |
| S02761583 | 0 | 21.57 | 0.69 | 67.41 | 0 |
| S02777420 | 100 | 0 | 1.02 | 24.19 | 0 |
| S02683120 | 44.79 | 0 | 0.24 | 10.17 | 0 |
| S02760983 | 38.36 | 0 | 0.76 | 77.62 | 0 |
| S02762229 | 0 | 1.71 | 0.91 | 47.3 | 0 |
| S02777327 | 100 | 0 | 0.19 | 87.16 | 0 |
| S02682782 | 0 | 0 | 0 | 84.32 | 0 |
| S02681470 | 0 | 15.56 | 0.54 | 64.3 | 0 |
| S02681254 | 0 | 17.13 | 0.83 | 67.3 | 0 |
| S02681701 | 95.71 | 0 | 3.16 | 84.77 | 0 |
| S02680988 | 23.72 | 0 | 0.9 | 86.66 | 0 |
| S02679122 | 13.19 | 0 | 1.17 | 85.62 | 0 |
| S02762134 | 7.79 | 0 | 0.44 | 44.62 | 0 |
| S02761824 | 92.14 | 0 | 1.79 | 87.81 | 0 |
| S02681181 | 0.7 | 0 | 0.83 | 88.36 | 0 |
| S02693243 | 100 | 0 | 0.28 | 90.49 | 0 |
| S02761563 | 79.66 | 0 | 3.11 | 90.32 | 0 |
| S02683055 | 48.63 | 0 | 0.48 | 90 | 0 |
| S02760954 | 5.37 | 0 | 1 | 82.8 | 0 |
| S02681857 | 96.32 | 0 | 4.19 | 79.25 | 0 |
| S02681715 | 24.34 | 0 | 3.52 | 83.21 | 0 |
| S02683164 | 20.42 | 0 | 0.44 | 82.79 | 0 |
| S02693285 | 16.74 | 0 | 0.91 | 91.81 | 0 |
| S02681877 | 46.02 | 0 | 2.16 | 42.23 | 0 |
| S02681516 | 10.55 | 0 | 1.39 | 64.86 | 0 |
| S02679236 | 19.81 | 0 | 1.15 | 87.73 | 0 |
| S02681529 | 67.18 | 0 | 1.67 | 82.39 | 0 |
| S02683015 | 45.03 | 0 | 0.31 | 89.46 | 0 |
| S02681822 | 37.48 | 0 | 0.2 | 55.6 | 0 |
| S02683023 | 52.91 | 0 | 0.43 | 88.35 | 0 |
| S02762060 | 60.92 | 0 | 0.72 | 52.15 | 0 |
| S02681288 | 58.22 | 0 | 1.77 | 73.06 | 0 |
| S02679516 | 39.2 | 0 | 1.43 | 78.89 | 0 |
| S02681011 | 48.14 | 0 | 0.84 | 80.09 | 0 |
| S02679127 | 61.15 | 0 | 0.71 | 76.43 | 0 |
| S02679614 | 55.98 | 0 | 0.62 | 82.44 | 0 |
| S02679734 | 46.13 | 0 | 0.64 | 81.62 | 0 |
| S02680909 | 55.93 | 0 | 0.39 | 72.45 | 0 |
| S02683105 | 100 | 0 | 0.19 | 0 | 68.67 |
| S02680839 | 100 | 0 | 0.36 | 0 | 27.17 |
| S02681102 | 100 | 0 | 0.19 | 0 | 17.38 |
| S02681264 | 0 | 15.27 | 0.49 | 54.31 | 0 |
| S02683035 | 42.86 | 0 | 0.36 | 89.76 | 0 |
| S02681129 | 82.19 | 0 | 0.6 | 87.3 | 0 |
| S02681689 | 5.72 | 0 | 0.48 | 59.87 | 0 |
| S02681475 | 10.63 | 0 | 0.33 | 60.45 | 0 |
| S02680984 | 29.15 | 0 | 0.37 | 85.14 | 0 |
| S02682855 | 17.65 | 0 | 0.53 | 74.34 | 0 |
| S02681708 | 100 | 0 | 0.71 | 75.66 | 0 |
| S02762013 | 100 | 0 | 0.32 | 30.07 | 0 |
| S02680910 | 31.26 | 0 | 0.42 | 78.19 | 0 |
| S02681709 | 95.37 | 0 | 3.86 | 74.09 | 0 |
| S02689527 | 31.06 | 0 | 0.25 | 63.93 | 0 |
| S02761611 | 100 | 0 | 0.14 | 31.82 | 0 |
| S02681741 | 31.64 | 0 | 1.52 | 68.12 | 0 |
| S02761580 | 100 | 0 | 0.55 | 75.92 | 0 |
| S02761635 | 100 | 0 | 0.16 | 39.86 | 0 |
| S02693315 | 100 | 0 | 0.34 | 51.14 | 0 |
| S02760951 | 100 | 0 | 0.21 | 60.96 | 0 |
| S02681101 | 57.32 | 0 | 0.43 | 82.13 | 0 |
| S02777203 | 78.65 | 0 | 0.77 | 67.36 | 0 |
| S02777086 | 66.96 | 0 | 0.8 | 66.72 | 0 |
| S02678934 | 89.8 | 0 | 1.25 | 48.1 | 0 |
| S02681463 | 63.85 | 0 | 1.88 | 77.67 | 0 |
| S02760943 | 60.05 | 0 | 0.6 | 68.64 | 0 |
| S02681851 | 67.27 | 0 | 1.79 | 69.19 | 0 |
| S02679504 | 74.69 | 0 | 0.5 | 56.83 | 0 |
| S02776856 | 63.74 | 0 | 0.81 | 65.81 | 0 |
| S02681889 | 75.9 | 0 | 1.11 | 63.37 | 0 |
| S02681924 | 71.35 | 0 | 1.18 | 61.48 | 0 |
| S02683143 | 2.14 | 0 | 0.61 | 12.52 | 0 |
| S02760958 | 75.38 | 0 | 0.56 | 82.01 | 0 |
| S02681811 | 49.11 | 0 | 0.23 | 12.78 | 0 |

TABLE 2-continued

This Table continues presenting the initial ERED variants used for the selection. The first column of Table 2 holds the record number corresponding to an ERED variant. The remaining columns show the fold-improvement over a positive control for the conversion of the substrates Dione_R (Column 8), Dione_S (Column 9), Dione-conv (Column 10), S-carvone_R (Column 11), and S-carvone_S (Column 12), to products.

| Col 1 | Col 8 | Col 9 | Col 10 | Col 11 | Col 12 |
|---|---|---|---|---|---|
| S02761104 | 55.26 | 0 | 0.46 | 63.34 | 0 |
| S02761644 | 100 | 0 | 0.15 | 27.64 | 0 |
| S02761602 | 100 | 0 | 0.16 | 30.64 | 0 |
| S02762215 | 100 | 0 | 0.16 | 56.46 | 0 |
| S02693267 | 100 | 0 | 0.2 | 52.66 | 0 |
| S02693321 | 29.64 | 0 | 0.38 | 50.81 | 0 |

The above data was used to run the selection method to obtain an optimal subset of 96 variants. The following parameters were used during the optimization: the population size (popSize) was 100; the number of generations (nGen) was 100; the crossover rate (crossrate) was 2; the mutation rate (mutrate) was 1%. There were no required samples. After 100 (nGen) generations the following optimized set of 96 (nvar) variants were obtained:

TABLE 3

The columns of the Table show the record ID, fitness, Pareto front membership, and niche count for the 96 variants that were selected.

| Record | Fitness | Front | Niche Count |
|---|---|---|---|
| S02680809 | 1.623 | 01 | 18.936 |
| S02689522 | 1.617 | 01 | 19.049 |
| S02747317 | 1.606 | 01 | 19.263 |
| S02683110 | 1.515 | 01 | 21.095 |
| S02681878 | 1.493 | 01 | 21.574 |
| S02681793 | 1.489 | 01 | 21.667 |
| S02747018 | 1.432 | 01 | 22.934 |
| S02747174 | 1.429 | 01 | 22.997 |
| S02747414 | 1.414 | 01 | 23.342 |
| S02747352 | 1.413 | 01 | 23.366 |
| S02760534 | 1.370 | 01 | 24.397 |
| S02681023 | 1.351 | 01 | 24.856 |
| S02680726 | 1.290 | 01 | 26.413 |
| S02762203 | 1.280 | 01 | 26.698 |
| S02683238 | 1.278 | 01 | 26.735 |
| S02681093 | 1.268 | 01 | 27.025 |
| S02681066 | 1.250 | 01 | 27.513 |
| S02683173 | 1.245 | 01 | 27.635 |
| S02683107 | 1.211 | 01 | 28.603 |
| S02682962 | 1.198 | 01 | 28.968 |
| S02681230 | 1.151 | 01 | 30.355 |
| S02681901 | 1.147 | 01 | 30.478 |
| S02681185 | 1.111 | 01 | 31.605 |
| S02681737 | 1.101 | 01 | 31.928 |
| S02760822 | 1.089 | 01 | 32.321 |
| S2681914 | 1.080 | 01 | 32.603 |
| S02682981 | 1.069 | 01 | 32.959 |
| S2681817 | 1.060 | 01 | 33.254 |
| S02760925 | 1.047 | 01 | 33.684 |
| S02683198 | 1.042 | 01 | 33.860 |
| S02680872 | 1.033 | 01 | 34.176 |
| S02679642 | 1.032 | 01 | 34.217 |
| S02761975 | 1.023 | 01 | 34.521 |
| S02683245 | 1.009 | 01 | 35.005 |
| S02681220 | 1.007 | 01 | 35.065 |
| S02760590 | 0.982 | 01 | 35.949 |
| S02681855 | 0.977 | 01 | 36.142 |
| S02760924 | 0.963 | 01 | 36.654 |
| S02683189 | 0.946 | 01 | 37.276 |
| S02681879 | 0.927 | 01 | 38.003 |
| S02760913 | 0.917 | 01 | 38.360 |
| S02680953 | 0.916 | 01 | 38.401 |
| S02693241 | 0.902 | 01 | 38.941 |

TABLE 3-continued

The columns of the Table show the record ID, fitness, Pareto front membership, and niche count for the 96 variants that were selected.

| Record | Fitness | Front | Niche Count |
|---|---|---|---|
| S02679726 | 0.901 | 01 | 38.984 |
| S02761906 | 0.901 | 01 | 39.000 |
| S02679574 | 0.898 | 01 | 39.125 |
| S02681426 | 0.893 | 01 | 39.295 |
| S02681730 | 0.867 | 01 | 40.325 |
| S02760937 | 0.865 | 01 | 40.417 |
| S02681487 | 0.854 | 01 | 40.884 |
| S02689613 | 0.848 | 01 | 41.124 |
| S02681796 | 0.845 | 01 | 41.218 |
| S02681670 | 0.842 | 01 | 41.377 |
| S02681828 | 0.839 | 01 | 41.495 |
| S02682781 | 0.824 | 01 | 42.117 |
| S02681531 | 0.817 | 01 | 42.410 |
| S02681474 | 0.803 | 01 | 43.013 |
| S02679696 | 0.801 | 01 | 43.106 |
| S02762167 | 0.793 | 01 | 43.441 |
| S02678915 | 0.792 | 01 | 43.464 |
| S02761717 | 0.790 | 01 | 43.582 |
| S02681340 | 0.789 | 01 | 43.617 |
| S02777077 | 0.787 | 01 | 43.722 |
| S02679477 | 0.778 | 01 | 44.107 |
| S02681774 | 0.777 | 01 | 44.126 |
| S02678918 | 0.775 | 01 | 44.208 |
| S02679586 | 0.767 | 01 | 44.566 |
| S02679646 | 0.758 | 01 | 44.977 |
| S02777496 | 0.756 | 01 | 45.089 |
| S02761978 | 0.747 | 01 | 45.461 |
| S02746981 | 0.745 | 01 | 45.553 |
| S02761627 | 0.743 | 01 | 45.685 |
| S02762113 | 0.738 | 01 | 45.906 |
| S02682933 | 0.735 | 01 | 46.025 |
| S02761830 | 0.726 | 01 | 46.440 |
| S02681451 | 0.725 | 01 | 46.517 |
| S02678987 | 0.721 | 01 | 46.688 |
| S02681038 | 0.719 | 01 | 46.776 |
| S02681662 | 0.718 | 01 | 46.838 |
| S02683108 | 0.707 | 01 | 47.354 |
| S02682810 | 0.704 | 01 | 47.486 |
| S02679399 | 0.698 | 01 | 47.785 |
| S02777468 | 0.697 | 01 | 47.837 |
| S02681080 | 0.687 | 01 | 48.286 |
| S02680675 | 0.679 | 01 | 48.683 |
| S02679281 | 0.676 | 01 | 48.854 |
| S02777061 | 0.670 | 01 | 49.112 |
| S02680858 | 0.665 | 01 | 49.375 |
| S02761741 | 0.660 | 01 | 49.607 |
| S02683061 | 0.659 | 01 | 49.674 |
| S02679508 | 0.649 | 01 | 50.176 |
| S02679296 | 0.645 | 01 | 50.390 |
| S02681896 | 0.635 | 01 | 50.857 |
| S02762197 | 0.620 | 01 | 51.623 |
| S02762065 | 0.608 | 01 | 52.265 |
| S02679244 | 0.595 | 01 | 52.964 |

The activities of the variants against the 11 objectives were presented in Tables 2 and 3.

The above list of variants can then be used to construct a screening panel which is expected to demonstrate optimized phenotypic diversity.

What is claimed is:

1. A computer program product comprising a non-transitory computer useable medium having a computer readable medium having program instructions for selecting an optimized, diverse set of molecular variants from a plurality of molecular variants, wherein the program instructions comprise:
(a) code for receiving an objective data set representing two or more properties of each molecular variant in a plurality of molecular variants;
(b) code for generating a first Pareto front membership of all molecular variants based on the one or more objectives for optimization;

(c) code for setting optimization parameters, wherein the optimization parameters comprise:
  (i) number nvar of molecular variants to create;
  (ii) a molecular variant population size popSize;
  (iii) a crossover rate crossrate;
  (iv) a mutation rate mutrate;
  (v) a fitness function comprising a penalty fitness function and an overall fitness function, wherein the penalty fitness is based on niche count and the overall fitness function is based on location in a descending Pareto front divided by the shared number of molecular variants within each front; and
  (vi) specific molecular variants to be included in the nvar of molecular variants; and
(d) code for identifying a search space of acceptable molecular variants;
(e) code for generating a random population of genomes from the search space of acceptable molecular variants by applying a selection operator; and
(f) code for applying a set of operators comprising a crossover operator, a mutation operator, a fitness operator, and a repair operator on the random plurality of genomes to select the nvar set of optimized, diverse molecular variants.

2. The computer program of claim 1 further comprising a code for repeating step (f) on a combined population of the first nvar set molecular variant and the molecular variant set popSize to generate a second nvar set of molecular variants.

3. A computer program product comprising a non-transitory computer useable medium a computer readable medium having program instructions for selecting an optimized, diverse set of molecular variants from a plurality of molecular variants, wherein the program instructions comprise:
  (a) code for receiving an objective data set representing two or more properties of each molecular variant in a plurality of molecular variants;
  (b) code for generating a first Pareto front membership of all molecular variants based on the one or more objectives for optimization;
  (c) code for setting optimization parameters, wherein the optimization parameters comprise:
    (i) number nvar of molecular variants to create;
    (ii) a molecular variant population size popSize;
    (iii) a crossover rate crossrate;
    (iv) number of generations to create nGen;
    (v) a mutation rate mutrate;
    (vi) a fitness function comprising a penalty fitness function and an overall fitness function, wherein the penalty fitness is based on niche count and the overall fitness function is based on the location of the molecular variant in a descending Pareto front divided by the shared number of molecular variants within each front; and
    (vii) specific molecular variants to be included in the nvar of molecular variants; and
  (d) code for identifying a search space of acceptable molecular variants;
  (e) code for generating a random population of genomes from the search space of acceptable molecular variants;
  (f) code for selecting a first set of genomes of size popSize from the random population, wherein each genome consisting of nvar molecular variants is created by applying a selection operator, a crossover operator, a mutation operator, a repair operator, and a fitness operator to the random population of genomes; and
  (g) code for returning the genome with the highest fitness as the final, optimized, diverse nvar set of molecular variants.

4. The computer program of claim 3 further comprising a code for repeating step (f) nGen times to select a new population of genomes of size popSize.

* * * * *